United States Patent
Xu et al.

(10) Patent No.: US 10,570,456 B2
(45) Date of Patent: Feb. 25, 2020

(54) CIRCULATING TUMOUR CELL TYPING AND IDENTIFICATION KIT

(71) Applicant: Surexam Bio-Tech Co., Ltd., Guangzhou (CN)

(72) Inventors: Jiasen Xu, Guangzhou (CN); Shiyang Wu, Guangzhou (CN); Suyan Liu, Guangzhou (CN)

(73) Assignee: Surexam Bio-Tech Co., Ltd. (CN)

( * ) Notice: Subject to any disclaimer, the term of this patent is extended or adjusted under 35 U.S.C. 154(b) by 0 days.

(21) Appl. No.: 15/113,010

(22) PCT Filed: Feb. 4, 2016

(86) PCT No.: PCT/CN2016/073508
§ 371 (c)(1),
(2) Date: Jul. 20, 2016

(87) PCT Pub. No.: WO2017/096714
PCT Pub. Date: Jun. 15, 2017

(65) Prior Publication Data
US 2017/0275696 A1    Sep. 28, 2017

(30) Foreign Application Priority Data
Dec. 10, 2015  (CN) .......................... 2015 1 0916641

(51) Int. Cl.
*C07H 21/04*   (2006.01)
*C07H 21/02*   (2006.01)
*C12Q 1/6886*  (2018.01)
*C12Q 1/6881*  (2018.01)

(52) U.S. Cl.
CPC ......... *C12Q 1/6886* (2013.01); *C12Q 1/6881* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| 6,110,678 A | * | 8/2000 | Weisburg | ............. | C12Q 1/6834 435/6.12 |
|---|---|---|---|---|---|
| 2014/0134646 A1 | | 5/2014 | Martin et al. | | |
| 2014/0308669 A1 | | 10/2014 | Yang et al. | | |

FOREIGN PATENT DOCUMENTS

| CN | 104031993 A | 9/2014 |
|---|---|---|
| CN | 104781007 A | 7/2015 |
| WO | 2007001986 A2 | 1/2007 |
| WO | 2009038754 A2 | 3/2009 |
| WO | 2011112903 A2 | 9/2011 |

OTHER PUBLICATIONS

Satelli (Clin Cancer Res, 21(4), 899-906).*
Gorges, Tobias et al., "Circulating tumor cells escape from EpCAM-based detection due to epithelial-to-mesenchymal transition", BMC Cancer 2012, 12:178, pp. 1-13.
Yicun Man et al., "Currently Used Markers for CTC Isolation—Advantages, Limitations and Impact on Cancer Prognosis", J. Clinic Experiment Pathol, 2011, 1:1, pp. 1-7.
Maenz et al., "Epithelial-mesenchymal plasticity is a decisive feature for the metastatic outgrowth of disseminated WAP-T mouse mammary carcinoma cells", BMC Cancer 2015, 15:178, pp. 1-10.
Barriere et al., "Circulating tumor cells and epithelial, mesenchymal and stemness markers: characterization of cell subpopulations", Annals of Translational Medicine 2014; 2(11), pp. 1-8.
International Search Report for PCT/CN2016/073508 dated Sep. 19, 2016.
Extended European Search Report and Written Opinion for EP16734165 dated Aug. 3, 2017.
International Preliminary Report on Patentablility for PCT/CN2016/073508 datd Sep. 19, 2016 (translation dated Dec. 1, 2016).

* cited by examiner

*Primary Examiner* — Sarae L Bausch
(74) *Attorney, Agent, or Firm* — Lerner, David, Littenberg, Krumholz & Mentlik, LLP

(57) ABSTRACT

This disclosure relates to a circulating tumour cell typing and identification kit, comprising a capture probe, an amplification probe, and a labeled probe for each marker gene mRNA, wherein the marker gene mRNA comprises the following two types: at least two epithelial cell marker gene mRNAs selected from the group consisting of EPCAM, E-cadherin, CEA, KRT5, KRT7, KRT17, and KRT20 mRNAs; and, at least two mesenchymal cell marker gene mRNAs selected from the group consisting of VIMENTIN, N-cadherin, TWIST1, AKT2, ZEB2, ZEB1, FOXC1, FOXC2, SNAI1 and SNAI2 mRNAs. This disclosure prevents false-positive results caused by, for example, possible presence of a number of non-neoplastic epithelial cells in peripheral blood, introduction of normal epithelial cells during blood sampling, and the like. Accordingly, it may be assured that cells detected with epithelial cell marker genes and/or mesenchymal cell marker genes are indeed circulating tumour cells, further improving accuracy and reliability of the detection results.

8 Claims, 1 Drawing Sheet
Specification includes a Sequence Listing.

CIRCULATING TUMOUR CELL TYPING AND IDENTIFICATION KIT

CROSS REFERENCE TO RELATED APPLICATIONS

The present application is a national phase entry under 35 U.S.C. § 371 of International Application No. PCT/CN2016/073508, filed Feb. 4, 2016, which claims priority from Chinese Patent Application No. 201510916641.6, filed Dec. 10, 2015, all of which are hereby incorporated herein by reference.

SEQUENCE LISTING

The instant application contains a Sequence Listing which has been submitted electronically in ASCII format and is hereby incorporated by reference in its entirety. Said ASCII copy, created on Jul. 19, 2016, is named 9ACIP 3.3F-028_SEQUENCE LISTING.txt and is 29,868 bytes in size.

TECHNICAL FIELD

The present disclosure belongs to the field of molecular biology, and relates to the medical sciences and biological technologies. More particularly, it relates to a circulating tumour cell typing and identification kit.

BACKGROUND

Circulating tumour cell (CTC) refers to collectively all types of tumour cells occurring in peripheral blood, which was detached from a solid tumour lesion (primary lesion or metastatic lesion) spontaneously or due to medical operations. After entering into peripheral blood, most CTCs ended in apoptosis or being devoured, while a few may escape and anchor to develop into a metastatic lesion, resulting in increased mortality risk of malignant tumour patients.

Research in recent years has revealed that tumour cells, during the process of entering peripheral blood (PB) circulation, may go through epithelial-mesenchymal transition (EMT). Tumour cells gone through epithelial-mesenchymal transition (EMT) have increased migration and invasion abilities. Some researchers detected the expression of CTC mesenchymal marker vimentin and epithelial marker Keratin mRNAs in metastatic NSCLC patients using immunofluorescent staining, wherein results indicating that strong co-expression of both markers were observed in nearly all CTCs. No CTCs that only expressed keratin mRNA were observed, while a few CTCs that only expressing vimentin mRNA were found in 3 patients. This study confirmed for the first time the existence of CTCs with mixed epithelial/mesenchymal phenotypes. The phenotype of NSCLC primary tumour is keratin mRNA positive and vimentin mRNA negative. In addition, other researchers have conducted assays for determining three EMT marker mRNAs (TWIST1, Akt2, PI3Kα) of CTCs in breast cancer patients using AdnaTest method, and found that 29% patients appeared positive for at least one of these markers. By analyzing the single cell transcriptional profiles of CTCs in breast cancer patients, researchers found that, despite of gene expression variations among CTCs, genes that involved in EMT, including TGF-β1, vimentin and CXCR4, are generally highly expressed in CTCs. Other studies also confirmed the highly frequent occurrence of co-expression of epithelial markers (EpCAM, cytokeratins, E-cadherin), mesenchymal markers (vimentin, N-cadherin, O-cadherin), and stem cell marker (CD133) in CTCs of tumour patients. In yet another study, researchers performed assays to determine expression of EMT-relevant transcription factor mRNAs (TWIST1, SNAIL1, SLUG, ZEB1, FOXC2) in breast cancer CTCs and analyzed potential influences of presence or absence of neoadjuvant chemotherapy on expression of such transcription factors in CTCs. They found that neoadjuvant chemotherapy did not eliminate these CTCs in which EMT had occurred. It was proposed that EMT probably provided the CTCs with tolerance to chemotherapy by endowing them with stem cell characteristics. Therefore, CTCs typing and identification may have great significance in guiding development of molecular targeted drugs and clinical individualized treatment.

Currently, most detection methods for CTCs use epithelial markers (such as epithelial cell adhesion molecule, EPCAM) as target spots, then capture CTCs with corresponding antibodies, and use CKs expressed on cells as a primary diagnostic indicator. Such methods involve EPCAM and CKs that are both specific for epithelial cells. A representative detection method in this regard is CellSearch system, which is the only one that is approved by USFDA for clinical application. False positive or false-negative detection results may occur due to the possible presence of a number of non-neoplastic epithelial cells in peripheral blood, potential contamination in blood samples by normal epithelial cells during blood sampling, and that some CTCs cannot be detected due to loss of epithelial antigens during EMT. Additionally, immunomagnetic separation (MACS) technique in combination with reverse transcriptase-polymerase chain reaction (RT-PCR) is also a commonly used CTC separation and identification technique. However, drawbacks exist as RT-PCR process has high requirements for environments and operation, mRNA is prone to degradation which disables CTC cell typing, and the like. Therefore, a technique for accurate detection, identification, and precise typing of CTCs is in urgent need.

SUMMARY OF DISCLOSURE

One goal of the present disclosure is to provide a circulating tumour cell typing and identification kit with strong specificity and high sensitivity.

A technical solution for achieving the aforementioned goal is disclosed as follows.

A circulating tumour cell typing and identification kit comprises a capture probe, an amplification probe, and a labeled probe for each marker gene mRNA, wherein the marker gene mRNA comprises the following two types: at least two epithelial cell marker gene mRNAs selected from the group consisting of EPCAM, E-cadherin, CEA, KRT5, KRT7, KRT17, and KRT20 mRNAs; and, at least two mesenchymal cell marker gene mRNAs selected from the group consisting of VIMENTIN, N-cadherin, TWIST1, AKT2, ZEB2, ZEB1, FOXC1, FOXC2, SNAI1, and SNAI2 mRNAs; wherein, the capture probe binds the marker gene mRNA to the amplification probe and has the following base composition from 5'-terminal to 3'-terminal in sequence: a specific sequence P1 for joining to the marker gene mRNA to be detected, a spacer arm sequence, and a P2 sequence, wherein there is no hairpin structure in the P2 sequence, no dimer or mispairing formed within or among the probes, no specific binding sequences between the P2 sequence and P1, P4, or the marker gene mRNA, and wherein the same P2 sequence is used for the capture probes for the marker genes of the same type;

the amplification probe has the following base composition from 5'-terminal to 3'-terminal in sequence: a P3 sequence that is able to complementarily pair with the P2 sequence of the corresponding capture probe, a spacer arm sequence, and a P4 sequence, wherein there is no hairpin structure in the P4 sequence, no dimer or mispairing formed within or among the probes, no specific binding sequences between the P4 sequence and P1, P2, P3, or total mRNA; and each labeled probe may have a P5 sequence that is able to complementarily pair with the P4 sequence of the corresponding amplification probe and a fluorescent group as a terminal modification, wherein different fluorescent groups are used to marker genes of different cell types.

In one of the embodiments, the marker gene mRNA may further comprise a type for leukocyte marker gene mRNA, wherein the leukocyte marker gene mRNA may be CD45. Use of leukocyte marker gene mRNA may assist further distinguishing leukocytes from tumour cells. Accordingly, interference of leukocytes to detection results is excluded to improve accuracy of results.

In one of the embodiments, within the capture probe for the epithelial cell marker gene, the P1 specific sequences for the EPCAM gene may be two or more selected from SEQ ID NO.1~SEQ ID NO.10, the P1 specific sequences for the E-cadherin gene may be two or more selected from SEQ ID NO.11~SEQ ID NO.20, the P1 specific sequences for the CEA gene may be two or more selected from SEQ ID NO.21~SEQ ID NO.30, the P1 specific sequences for the KRT5 gene may be two or more selected from SEQ ID NO.31~SEQ ID NO.40, the P1 specific sequences for the KRT7 gene may be two or more selected from SEQ ID NO.41~SEQ ID NO.50, the P1 specific sequences for the KRT17 gene may be two or more selected from SEQ ID NO.51~SEQ ID NO.60, and the P1 specific sequences for the KPT20 gene may be two or more selected from SEQ ID NO.61~SEQ ID NO.70; the P2 sequence of the capture probe for the epithelial cell marker genes may be SEQ ID NO.181; and within the amplification probes for the epithelial cell marker gene mRNAs, the P3 sequence may be SEQ ID NO.184 and the P4 sequence may be SEQ ID NO.187.

In one of the embodiments, within the capture probe for the mesenchymal cell marker gene, the P1 specific sequences for the VIMENTIN gene may be two or more selected from SEQ ID NO.71~SEQ ID NO.80, the P1 specific sequences for the N-cadherin gene may be two or more selected from SEQ ID NO.81~SEQ ID NO.90, the P1 specific sequences for the TWIST1 gene may be two or more selected from SEQ ID NO.91~SEQ ID NO.100, the P1 specific sequences for the AKT2 gene may be two or more selected from SEQ ID NO.101~SEQ ID NO.110, the P1 specific sequences for the ZEB2 gene may be two or more selected from SEQ ID NO.111~SEQ ID NO.120, the P1 specific sequences for the ZEB1 gene may be two or more selected from SEQ ID NO.121~SEQ ID NO.130, the P1 specific sequences for the FOXC1 gene may be two or more selected from SEQ ID NO.131~SEQ ID NO.140, the P1 specific sequences for the FOXC2 gene may be two or more selected from SEQ ID NO.141~SEQ ID NO.150, the P1 specific sequences for the SNAI1 gene may be two or more selected from SEQ ID NO.151~SEQ ID NO.160, the P1 specific sequences for the SNAI2 gene may be two or more selected from SEQ ID NO.161~SEQ ID NO.170; the P2 sequence of the capture probe for the mesenchymal cell marker genes may be SEQ ID NO.182; and within the amplification probes for the mesenchymal cell marker gene mRNAs, the P3 sequence may be SEQ ID NO.185 and the P4 sequence may be SEQ ID NO.188.

In one of the embodiments, within the capture probe for the leukocyte cell marker gene mRNAs, the P1 specific sequences for the CD45 gene may be two or more selected from SEQ ID NO.171~SEQ ID NO.180; the P2 sequence of the capture probe for the leukocyte cell marker gene may be SEQ ID NO.183; and within the amplification probes for the leukocyte cell marker gene mRNA, the P3 sequence may be SEQ ID NO.186 and the P4 sequence may be SEQ ID NO.189.

In one of the embodiments, the spacer arm sequence may be 5-10T.

In one of the embodiments, the fluorescent group may be selected from the group consisting of: FAM, TET, JOE, HEX, Cy3, TAMRA, ROX, Texas Red, LC RED640, Cy5, LC RED705, and Alexa Fluor 488, and wherein different fluorescent groups are used for marker genes of different cell types.

The primary advantages of the present disclosure include:

(1) The epithelial marker genes and mesenchymal marker genes provided in this disclosure were selected by the inventors through numerous experiments, comprehensive assessment, statistical analysis, and optimized combination of a plurality of parameters. The marker genes of the present disclosure are chosen not only to detect single marker gene, but may also used with other marker genes to comprehensively detect circulating tumour cells and identify the cell types. Accordingly, false-negative results due to variation in expression levels of certain marker genes among individual circulating tumour cells are avoided, and detection sensitivity is greatly improved.

(2) The identification method of the present disclosure uses a multiple RNA probe, which can label a plurality of CTC specific genes simultaneously and identify the cell types as Type I (the epithelial type), Type II (the mixed epithelial-mesenchymal type), and Type III (the mesenchymal type), reducing false-negative results due to loss of some CTC specific genes during the process of CTCs entering peripheral blood circulation. The variety of probes designed in the present disclosure may go through hybridization under homogeneous reaction conditions, while there is substantially no non-specific binding among different types of probes. The probes designed herein show good specificity and high signal to noise ratio in an assay. Additionally, multiple probes used in combination allow the identification kit and method to form a system with ideal detection results. The present disclosure employs multi-site specific pairing of probes and cascade amplification, instead of PCR amplification, to amplify the signals, which improves detection signal and detection specificity and avoids false-negative resulted from reverse-transcription PCR and real-time fluorescence quantification PCR technologies.

(3) One disadvantage of RNA in situ hybridization method is low sensitivity of fluorescent signals. However, the present disclosure utilizes a novel RNA in situ hybridization method so that the intensity of fluorescent signals is improved via a signal amplification system. The detection process of the present disclosure may be completed in 8 hours, while a single copy of mRNA hybridization probe is coupled to a corresponding fluorescence probe via the signal amplification system, significantly improving the sensitivity of RNA in situ hybridization.

DETAILED DESCRIPTION OF EMBODIMENTS

Figure 1:
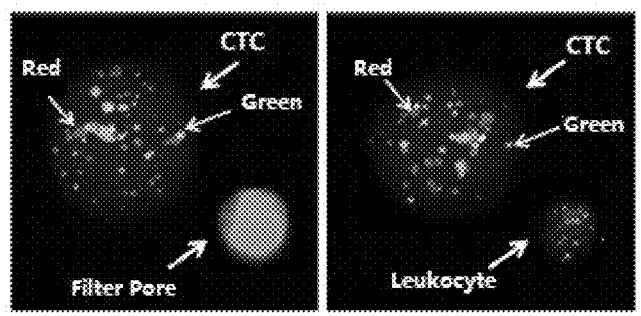
FIG. 1 shows a graph of positive CTC identification results in an embodiment of the present disclosure.

To facilitate understanding of the present disclosure, a more comprehensive description is provided below. The disclosure as disclosed herein may be implemented in various forms and not limited to the embodiments described herein, which are, on the contrary, provided only for the purpose of facilitating thorough and complete understanding of the present disclosure.

Experimental methods in the following embodiments, if specific conditions are not explicitly indicated, generally follow routine conditions, such as described in, e.g., Sambrook et al., Molecular Cloning: A Laboratory Manual, New York: Cold Spring Harbor Laboratory Press, 1989, or follow conditions recommended by the manufacturer. The various common chemical reagents used in the embodiments are all commercially available.

Unless indicated otherwise, all the technical and scientific terms used in the present disclosure have the same meaning as generally comprehended by a person skilled in the art. The term employed in the present description is only for the purpose of illustrating specific embodiments and not in any aspect to limit the scope of the present disclosure. The term "and/or" as used herein means to comprise any and all combination of one or more of the referenced items.

A process for typing and identification of circulating tumour cells, mainly comprising the following steps:

(1) obtaining a biological fluid sample with red blood cells removed;

(2) filtering and enriching circulating tumour cells using a filter membrane, and then permeabilizing and digesting CTCs to expose mRNA;

(3) detecting the presence of epithelial cell marker gene mRNA and/or mesenchymal cell marker gene mRNA, wherein the epithelial cell marker genes are two or more selected from the group consisting of EPCAM, E-cadherin, CEA, KRT5, KRT7, KRT17, and KRT20; and the mesenchymal cell marker genes are two or more selected from the group consisting of VIMENTIN, N-cadherin, TWIST1, AKT2, ZEB2, ZEB1, FOXC1, FOXC2, SNAI1, and SNAI2;

the step of detecting the presence of epithelial cell marker gene mRNA and/or mesenchymal cell marker gene mRNA comprises following steps:

(3.1) a P1 specific sequence of a capture probe of each marker gene binding to a corresponding target marker gene; each capture probe being, from 5'-terminal to 3'-terminal, consisted sequentially of: a specific sequence P1 for joining to the marker gene mRNA to be detected, a spacer arm sequence, and a P2 sequence that is able to complementarily pair with a P3 sequence of a corresponding amplification probe, wherein there is no hairpin structure in the P2 sequence, no dimer or mispairing formed within or among the probes, no specific binding sequences between the P2 sequence and P1, P4, or the marker gene mRNA;

(3.2) the P2 sequence of the capture probe specifically binding to a P3 sequence of an amplification probe; the amplification probe being, from 5'-terminal to 3'-terminal, consisted sequentially of: a P3 sequence that is able to complementarily pair with the P2 sequence of the capture probe, a spacer arm sequence, and a P4 sequence, wherein there is no hairpin structure in the P4 sequence, no dimer or mispairing formed within or among the probes, no specific binding sequences between the P4 sequence and P1, P2, P3, or total mRNA;

(3.3) the P4 sequence of the amplification probe specifically binding to a P5 sequence of a labeled probe with a fluorescent group as a terminal modification, so that a target mRNA signal is amplified in cascade, wherein different fluorescent groups are used for marker genes of different cell types;

(3.4) detecting via a fluorescence detector.

In one of the embodiments, the step of detecting the presence of epithelial cell marker gene mRNA and/or mesenchymal cell marker gene mRNA comprises following steps:

(3.1) a P1 specific sequence of a capture probe of each marker gene binding to a corresponding target marker gene; each capture probe being, from 5'-terminal to 3'-terminal, consisted sequentially of: a specific sequence P1 for joining to the marker gene mRNA to be detected, a spacer arm sequence, and a P2 sequence that is able to complementarily pair with a P3 sequence of a corresponding amplification probe, wherein there is no hairpin structure in the P2 sequence, no dimer or mispairing formed within or among the probes, no specific binding sequences between the P2 sequence and P1, P4, or the marker gene mRNA;

(3.2) the P2 sequence of the capture probe specifically binding to a P3 sequence of an amplification probe, the P3 sequence labeled with a fluorescent group, so that a target mRNA signal is amplified in cascade; the amplification probe being, from 5'-terminal to 3'-terminal, consisted sequentially of: a P3 sequence that is able to complementarily pair with the P2 sequence of the capture probe, a spacer arm sequence, and a P4 sequence, wherein there is no hairpin structure in the P4 sequence, no dimer or mispairing formed within or among the probes, no specific binding sequences between the P4 sequence and P1, P2, P3, or total mRNA;

(3.3) detecting via a fluorescence detector.

EXAMPLE 1

The circulating tumour cell typing and identification kit disclosed in this example can take two forms, either with or without a labeled probe.

A circulating tumour cell typing and identification kit A with a labeled probe mainly comprises:

I. Capture Probe

A capture probe consists of three components from 5'-terminal to 3'-terminal in sequence: a sequence P1 which complementarily pairs with corresponding marker gene mRNA, a spacer arm sequence, and a P2 sequence that is able to complementarily pair with a P3 sequence of a corresponding amplification probe, wherein the same P2 sequence is used in capture probes for marker genes of the same type. The spacer arm separates the P2 sequence of a capture probe from the target mRNA. A spacer arm sequence of appropriate length is usually provided within a probe to reduce steric hindrance and improve hybridization efficiency and specificity. The spacer arm of a capture probe of the present disclosure is preferably 5-10T, and more preferably 5T in this example. Ten capture probes are designed for each marker gene to increase detection specificity. (In use, detection for each target gene can be accomplished with two or more selected capture probes with excellent specificity and consistency. Please refer to, for example, Example 8.) This example preferably uses 10 capture probes to achieve best specificity. The capture probes for corresponding marker genes are listed in Table 1 and the P2 sequences of the capture probes for different types of marker genes are listed in Table 2.

TABLE 1

P1 sequence of a capture probe for a target gene

| Gene | P1 sequence of capture probe (5'→3') | SEQ ID NO. |
|---|---|---|
| EPCAM | CTCTCATCGCAGTCAGGATC | 1 |
| | ACACATTCTTCCTGAGCTGC | 2 |
| | AGCCATTCATTTCTGCCTTC | 3 |
| | TGATCCAGTAGGTTCTCACT | 4 |
| | CAGTTGATAACGCGTTGTGA | 5 |
| | AATAAGCCACATCAGCTATG | 6 |
| | TGACCAGGATCCAGATCCAG | 7 |
| | GCCATTCTCTTCTTTCTGGA | 8 |
| | CATTTGTAATTTGTGTCCAT | 9 |
| | CACTATTACAAATATATGAT | 10 |
| E-cadherin | CTTCTGAGGCCAGGAGAGGA | 11 |
| | CTTCTTTGTCTTTGTTGGAT | 12 |
| | TCTCTATCCAGAGGCTCTGT | 13 |
| | TCCATTGGATCCTCAACTGC | 14 |
| | GTAGGTGTTCACATCATCGT | 15 |
| | CCACCAGGGTATACGTAGGG | 16 |
| | CTCGTTCTCAGGCACCTGAC | 17 |
| | GTATGAACAGCTGTGAGGAT | 18 |
| | TCATTCACATCCAGCACATC | 19 |
| | TCCGGATTAATCTCCAGCCA | 20 |
| CEA | GTGTCATTCTGGATGATGTT | 21 |
| | GTATACCCGGAACTGGCCAG | 22 |
| | CTGATTGTTTACCCACCACA | 23 |
| | AGAGGACATTCAGGATGACT | 24 |
| | AGTCCCATTGACAAACCAAG | 25 |
| | GGCCAGTGTCTGAGTTATGG | 26 |
| | GCTCTGCATAGACTGTGATC | 27 |
| | CATAGGGTCCTACATCATTC | 28 |
| | GTGATGTTGGAGATAAAGAG | 29 |
| | GGTTGTGTTCTGAGCCTCAG | 30 |
| KRT5 | AAGCACCCGCAAGGCTGACC | 31 |
| | CCACCTCCAAAGCCATAGCC | 32 |
| | CAGGTTCTGCCTCACAGTCT | 33 |
| | AAGCCAGGGCCACCGAAGCC | 34 |
| | GGTCCTCACCCTCTGGATGC | 35 |
| | TTGTTCTGCTGCTCCAGGAA | 36 |
| | TGTCAATCTCGGCTCTCAGC | 37 |
| | CATGTAGGCAGCATCTACAT | 38 |
| | TTGTCCATGGAGAGGACCAC | 39 |
| | CTCAGCGATGATGCTATCCA | 40 |
| KRT7 | CTTGTCGATGAAGGAGGCAA | 41 |
| | CCTGCAGTGCCTCAAGCTGA | 42 |
| | CTTCGTACTTATTCTTGAAG | 43 |
| | CCTTGCTCATGTAGGCAGCA | 44 |
| | AGGAAGTTGATCTCATCATT | 45 |
| | CTGCAGCTCTGTCAACTCCG | 46 |
| | GCAGTCCTTTAGGCACCTGT | 47 |
| | TCCGGGTATTCCGGAGGTCG | 48 |
| | TCGATGTCCAGGGCCAGCTT | 49 |
| | GCCGTGCCATATCCTGCTTG | 50 |
| KRT17 | TACTGAGTCAGGTGGGCATC | 51 |
| | TGCTGCTCCATCTCGCAGCG | 52 |
| | TGCTTTCATGCTGAGCTGGG | 53 |
| | CCAGCTCACTGTTGGTGGCC | 54 |
| | ATCTTCTCATACTGGTCACG | 55 |
| | ACATTGATCTCACCACCCAC | 56 |
| | GCCAGGGTCAGCTCATCCAG | 57 |
| | ACTCAGGCGCAGGGCCTGCT | 58 |
| | TCCTCAATTGTCCTGTAGTA | 59 |
| | AGCTGTAGCAGCTGGAGTAG | 60 |
| KRT20 | CAGGCAATTTGCAGCTCCTC | 61 |
| | GCTGATTCTTGCAGGGAGC | 62 |
| | ATGACACGACCTTGCCATCC | 63 |
| | TTCTCCTTCCAGAAGGCGGC | 64 |
| | GAAGGATATGGTATTCGTTG | 65 |
| | ACTGGAGGTTGGCTAACTGG | 66 |
| | GTCTGCAGCTCCGTTAGTTGA | 67 |
| | AAGGTTCTTCTGGGCCATGA | 68 |
| | TAGGCCATCGACTTCCTCCT | 69 |
| | TTCAGGCCTTGGAGATCAGC | 70 |
| vimentin | CAGAGGAGCGCGTGGCATAC | 71 |
| | CACCGAGTCCTGCAGGAGCC | 72 |
| | GTTGGCGAAGCGGTCATTCA | 73 |
| | AGGATCTTATTCTGCTGCTC | 74 |
| | GGTCCACCTGCCGGCCGAGC | 75 |
| | TGTCGCGCTCCACCTCGACG | 76 |
| | GCAGGCGGCCAATAGTGTCT | 77 |
| | GATTCCACTTTGCGTTCAAG | 78 |
| | AGCCACACTTTCATATTGCT | 79 |
| | CAAACTTGGATTTGTACCAT | 80 |
| N-cadherin | CCTGGTGTAAGAACTCAGGT | 81 |
| | CGGTCATCACATATGTTCCA | 82 |
| | GCTGCCACTGTGATGATGTC | 83 |
| | GGAGGATTGTCATTGACATC | 84 |
| | TGATCCTTATCGGTCACAGT | 85 |
| | ATTCCCTTGGCTAATGGCAC | 86 |
| | TGGCGAATGATCTTAGGATT | 87 |
| | CATTAAGCCGAGTGATGGTC | 88 |
| | TCCTGTCCACATCTGTGCAG | 89 |
| | GAGCAGGATGGCAATGATGG | 90 |
| TWIST1 | GTAGCTGAGCCGCTCGTGA | 91 |
| | TGGAGTCCAGCTCGTCGCT | 92 |
| | CTGAATCTTGCTCAGCTTG | 93 |
| | GAGGGCAGCGTGGGGATGA | 94 |
| | ACGCCTCGTTCAGCGACTG | 95 |
| | TGCGCTGGCGCTCCCGCAC | 96 |
| | GCTGCGTCTGCAGCTCCTC | 97 |
| | AGACTTCTATCAGAATGCA | 98 |
| | AGTTATCCAGCTCCAGAGT | 99 |
| | TTCTCTGGAAACAATGACA | 100 |
| AKT2 | GCAGGCAGCGTATGACAAAG | 101 |
| | CACCAGGATGACTTTGCCAA | 102 |
| | TTCAGCGCAGTGAGGAACGG | 103 |
| | GCACAGGCGGTCGTGGGTCT | 104 |
| | GAGCCGAGACAATCTCTGCA | 105 |
| | ATCTTTGTCCAGCATGAGGT | 106 |
| | AGGCGCTCGTGGTCCTGGTT | 107 |
| | CAAGCAGGGACTTGGCCTCG | 108 |
| | CTCCGGGGTCCCACAGAAGG | 109 |
| | GACCTCGGACGTGACCTGAG | 110 |
| ZEB2 | CTCCCGCTTGCAGTAGGAAT | 111 |
| | GAGTGCTCGATAAGGTGGTG | 112 |
| | CACATAAGTCACATGCATAC | 113 |
| | AGACAGGAGTCGGAGTCTGT | 114 |
| | GTAGCTGCTCCAGTTGGGTA | 115 |
| | ATGCTGAACACTGGGTTAGT | 116 |
| | TATGATCTAAACTGATGCTA | 117 |
| | TTGGTAATGACAAGTCTAAA | 118 |
| | GAGAGGAGGATCACAATTCG | 119 |
| | TCTGCTATAGATGGTGATGT | 120 |
| ZEB1 | TGAAAGATCAAGAGGTTCTA | 121 |
| | TGTACTACTTCTGGAACCAT | 122 |
| | GGCTGATCATTGTTCTTGGC | 123 |
| | GAGAGCTCTTCTGCACTTGG | 124 |
| | GCCATCTCCAGTAGCTGATG | 125 |
| | AGGCTGCTTTAGGTCATAGT | 126 |
| | GGACAATCATCACACAGAAG | 127 |
| | TAACAGAATGGCCACCTTGT | 128 |
| | ATGCAAGATTGGCTTGATTA | 129 |
| | CCAACTGTTGGCAGAACAAC | 130 |
| FOXC1 | TTTAGGTGGAGAATAGGTAA | 131 |
| | AACAATGAATATGTTCAACA | 132 |
| | CTTACGTGTTATCTGGAGTA | 133 |
| | TGGAGGGATATTCTGTTCGC | 134 |
| | TCCGGACGTGCGTACAGAG | 135 |
| | CACCGAGTGGAAGTTCTGCT | 136 |

TABLE 1-continued

P1 sequence of a capture probe for a target gene

| Gene | P1 sequence of capture probe (5'→3') | SEQ ID NO. |
|---|---|---|
| | CTGGTTCAGGTACCACGAGG | 137 |
| | GACGACGAGCTGCTGCTGGT | 138 |
| | TACAGGCTCATGGCTTGCAG | 139 |
| | CGCAGCGACGTCATGATGTT | 140 |
| FOXC2 | ACACATATACCCACCTGTGT | 141 |
| | AGGTAAGTACAACGATTAAG | 142 |
| | AATTATATCTCATAATTGTA | 143 |
| | AATGGCTCTGAACAACAACA | 144 |
| | TCAGGTCGAGCACAGCACAG | 145 |
| | AGCTGGCATTGCCACTCACC | 146 |
| | GCTCGCATGCTGCACTGGTA | 147 |
| | GCTCAGCGTCTCCACCTTGG | 148 |
| | CTCCTTGGACACGTCCTTCT | 149 |
| | CGAAGCACTCGTTGAGCGAG | 150 |
| SNAI1 | CGGACCCACACTGGTACGTG | 151 |
| | AAGCTGTGGACACTGAGGCC | 152 |
| | CCGGTACCTGCTAAACTCTC | 153 |
| | ACTTTATAGTAATTTATTAT | 154 |
| | GGAGAGTGACAGTTGAGGGA | 155 |
| | CCTGACCTCTGAGCGGTGAG | 156 |
| | TATTCGACTAAGGCTACCCA | 157 |
| | GGCATGGCTGAGACACAGAA | 158 |
| | CTGGTCTTACAAATGGACTC | 159 |

TABLE 1-continued

P1 sequence of a capture probe for a target gene

| Gene | P1 sequence of capture probe (5'→3') | SEQ ID NO. |
|---|---|---|
| | TAATGGCAGAGTGGAGTAGT | 160 |
| SNAI2 | CAACATCTCAGTTTCATACA | 161 |
| | ATTGCATTTGTGGTATGCAT | 162 |
| | AGACAATGGAGCATGCGCCA | 163 |
| | ACCTGAGTTCGCGTCTGGCA | 164 |
| | TCTCTCAATCTAGCCATCAG | 165 |
| | TGCATTCTGTTCGAGTAAAC | 166 |
| | TTGTGCAGGAGAGACATTCT | 167 |
| | GTCTGCAAATGCTCTGTTGC | 168 |
| | TCCGAATATGCATCTTCAGG | 169 |
| | GCTTGGACTGTAGTCTTTCCT | 170 |
| CD45 | GAAGTGCTGCAATGTGTCAT | 171 |
| | ACATGACTGTCTCCATGACA | 172 |
| | GAAGTTGAAGCTGGAAATAC | 173 |
| | GAGTCGCATAAGAATTGCGA | 174 |
| | AGGAAGACTTTTTCTGGCTG | 175 |
| | CCTATAAAGGAAGCTCGAAA | 176 |
| | AATGCCAGCTATATTGATGG | 177 |
| | GGAAATACATTGCTGCACAA | 178 |
| | TTGCTCCTCAAACTGAGAAG | 179 |
| | GATGCCTGATGGTTCAAGTA | 180 |

TABLE 2

P2 sequence of a capture probe for a target gene

| Type | Gene | P2 sequence of capture probe (5'→3') | SEQ ID NO. |
|---|---|---|---|
| Epithelial cell marker gene | EPCAM, E-cadherin, CEA, KRT5, KRT7, KRT17, KRT20 | GTAGCTTAGTCTGAAGTCAATACT | 181 |
| Mesenchymal cell marker gene | VIMENTIN, N-cadherin, TWIST1, AKT2, ZEB2, ZEB1, FOXC1, FOXC2, SNAI1, SNAI2 | ATTCATGACTATATTCTGTAGCAA | 182 |
| Leukocyte marker gene | CD45 | GTCAATGATGATCTTGGTATCTTG | 183 |

II. Amplification Probe

An amplification probe is a sequence that links a capture probe and a signal detection component and consists of three components: a P3 sequence at the 5'-terminal that is able to complementarily pair with the P2 sequence of the capture probe, a spacer arm sequence, and a P4 sequence at the 3'-terminal that is able to complementarily pair with the labeled probe (In case that the detection is performed without a labeled probe, the P4 sequence is modified with a fluorescent group at the 3'-terminal. See e.g., the kit B). The spacer arm sequence is formed in the middle with a length of 5 T (The spacer arm of a capture probe of the present disclosure is preferably 5-10 T, and more preferably 5 T in this example).

The P3 sequences of the amplification probes for marker genes are listed in Table 3. There is no hairpin structure in the P4 sequence, no dimer or mispairing formed within or among the probes, no specific binding sequences between the P4 sequence and P1, P2, P3, or total mRNA. Preferred base compositions for the P4 sequences in this embodiment are listed in Table 4.

TABLE 3

P3 sequence of an amplification probe for a target gene

| Type | Gene | P3 sequence of amplification probe (5'→3') | SEQ ID NO. |
|---|---|---|---|
| Epithelial cell marker gene | EPCAM, E-cadherin, CEA, KRT5, KRT7, KRT17, KRT20 | AGTATTGACTTCAGACTAAGCTAC | 184 |
| Mesenchymal cell marker gene | VIMENTIN, N-cadherin, TWIST1, AKT2, ZEB2, ZEB1, FOXC1, FOXC2, SNAI1, SNAI2 | TTGCTACAGAATATAGTCATGAAT | 185 |
| Leukocyte marker gene | CD45 | CAAGATACCAAGATCATCATTGAC | 186 |

TABLE 4

P4 sequence of an amplification probe for a target gene

| Type | Gene | P4 sequence of an amplification probe | SEQ ID NO. |
|---|---|---|---|
| Epithelial cell marker gene | EPCAM, E-cadherin, CEA, KRT5, KRT7, KRT17, KRT20 | GTACGTCGTAATTTGAATCTGTAG | 187 |
| Mesenchymal cell marker gene | VIMENTIN, N-cadherin, TWIST1, AKT2, ZEB2, ZEB1, FOXC1, FOXC2, SNAI1, SNAI2 | GCTGTGAATGTAACATGTCTATCG | 188 |
| Leukocyte marker gene | CD45 | GTCAGTTAGACTATTGTTCGTTCG | 189 |

III. Labeled Probe

A labeled probe consists of two components: a P5 sequence at 5'-terminal that is able to complementarily pair with the P4 sequence of the corresponding capture probe and a fluorescent group at 3'-terminal as a label, so that a target mRNA signal is amplified in cascade via specifically binding to the P4 sequence of the amplification probe. (In case that the detection is performed with a labeled probe, a fluorescent group is not present at the 3'-terminal of the P4 sequence but the 3'-terminal of the labeled probe. See e.g., the kit A). The fluorescent group of the labeled probe may be selected from the group consisting of: FAM, TET, JOE, HEX, Cy3, TAMRA, ROX, Texas Red, LC RED640, Cy5, LC RED705, and Alexa Fluor 488. The fluorescent groups, and the colors or emission wavelengths thereof, selected for FL1, FL2, and FL3 of the labeled probes are different from each other, so as to distinguish marker genes of different types. Preferred fluorescent groups for the labeled probes in this embodiment are shown in Table 6.

TABLE 6

Labeled probe

| Type | Gene | P5 sequence of labeled probe | SEQ ID NO. | Fluorescent group |
|---|---|---|---|---|
| Epithelial cell marker gene | EPCAM, E-cadherin, CEA, KRT5, KRT7, KRT17, KRT20 | CTACAGATTCAAATTACGACGTAC | 190 | Cy3 Red fluorescent signal |
| Mesenchymal cell marker gene | VIMENTIN, N-cadherin, TWIST1, AKT2, ZEB2, ZEB1, FOXC1, FOXC2, SNAI1 | CGATAGACATGTTACATTCACAGC | 191 | Alexa Fluor488 Green fluorescent signal |

TABLE 6-continued

| | | Labeled probe | | |
|---|---|---|---|---|
| Type | Gene | P5 sequence of labeled probe | SEQ ID NO. | Fluorescent group |
| Leukocyte marker gene | CD45 | CGAACGAACAATAGTCT AACTGAC | 192 | Cy5 Purple fluorescent signal |

The circulating tumour cell typing and identification kit B without a labeled probe of this embodiment mainly comprises:

I. Capture probe: The capture probe is the same as that of a circulating tumour cell typing and identification kit with a labeled probe.

II. Amplification probe: The amplification probe is the same as that of a circulating tumour cell typing and identification kit with a labeled probe, except for a modification of a fluorescent group at the 3'-terminal thereof.

The 3'-terminal of the P4 sequence is modified with a fluorescent group. Specifically, a fluorescent group modification for a P4 sequence of an epithelial cell marker gene detection probe is called FL1, a fluorescent group modification for a P4 sequence of a mesenchymal cell marker gene detection probe called FL2, and a fluorescent group modification for a P4 sequence of an leukocytel marker gene detection probe called FL3. The fluorescent groups may be selected from the group consisting of: FAM, TET, JOE, HEX, Cy3, TAMRA, ROX, Texas Red, LC RED640, Cy5, LC RED705, and Alexa Fluor 488. The fluorescent groups, and the colors or emission wavelengths thereof, selected for FL1, FL2, and FL3 of the labeled probe are different from each other, so as to distinguish marker genes of different types. Preferred 3'-fluorescent groups for the P4 sequences of the marker gene amplification probes are shown in Table 5.

TABLE 5

| Dye label of a marker gene | | |
|---|---|---|
| Type | Marker gene | Modified fluorescent group |
| Epithelial cell marker gene | EPCAM、E-cadherin、CEA、KRT5、KRT7、KRT17、KRT20 | Cy3 Red fluorescent signal |
| Mesenchymal cell marker gene | VIMENTIN、N-cadherin、TWIST1、AKT2、ZEB2、ZEB1、FOXC1、FOXC2、SNAI1、SNAI2 | Alexa Fluor488 Green fluorescent signal |
| Leukocyte marker gene | CD45 | Cy5 Purple fluorescent signal |

EXAMPLE 2

Detection of Circulating Tumour Cells in Peripheral Blood of Tumour Patients Using the Kit A According to Example 1

The formulations of the various solutions are listed below:

| Name of solution | Formulation |
|---|---|
| Preserving solution | 16.6 g NH4Cl, 2 g KHCO3, 8 ml 0.5M EDTA, filled to 1 L with ultrapure water |
| Fixing agent | 10% Neutral formalin |
| PBS | 2.9 g Na2HPO4•12H2O, 0.3 g NaH2PO4•2H2O, 8.06 g NaCl, 0.2 g KCl, filled to 1000 ml with ultrapure water, pH7.4 |
| Permeabilization agent | 0.25% TritonX-100 |
| Digestive enyzme | 1 ug/ml proteinase K |
| Probe buffer solution | 100 µg/ml denatured salmon sperm DNA, 100 mM LiCl, 0.1% sodium dodecyl sulfate, 9 mM EDTA, 50 mM HEPES (pH 7.5), 0.05% ProClin 300 |
| Amplification buffer solution | 6 mM Tris-HCl (pH 8.0), 1% sodium dodecyl sulfate, 1 mL/L bovine serum albumin, 0.05% ProClin 300, 0.05% sodium azide |
| Color-developing buffer solution | 20 mM Tris-HCl, 400 mM LiCl, 1 mL/L Tween 20, 1 mL/L bovine serum albumin, 0.05% ProClin 300 |
| Probe mixture solution | i.e., capture probe, 0.75 fmol/ul/gene |
| Amplification mixture solution | i.e., amplification probe, 0.66 fmol/ul/gene |
| Color-developing mixture solution | i.e., labeled probe, 0.33 fmol/ul/gene |

Each of the probe mixture solution, amplification mixture solution, and color-developing mixture solution in this example employs all the probes shown in the tables of corresponding genes for the circulating tumour cell typing and identification kit A with a labeled probe according to Example 1.

I. Sample Preparation: Filtration of CTCs onto a Filter Membrane

1. A blood sample was preserved in a sample storage tube with the preserving solution, centrifuged horizontally at 600×g for 5 min. Then, the supernatant was discarded and the red blood cells were removed.

2. 4 ml PBS and 1 ml fixative were added, vortex-mixed evenly, and allowed to stand at room temperature for 8 min.

3. Sample Filtration: the fluid in the sample storage tube was transferred to a filter and all the fluid was filtered by turning on a vacuum filtration pump; 4 ml PBS was added to the sample storage tube to wash the tube walls before vacuum filtration was conducted again for the wash fluid.

4. The filter membrane was transferred to a 24-well plate, 400 µl 4% formaldehyde solution was added, and then fixed at room temperature for 1 h.

5. The liquid was removed, washed three times with 1 ml PBS per well, soaking for 2 min each time.

II. Permeabilization Treatment

1. In a new 24-well plate, 50 µl permeabilizing agent was added to each well. The filter membrane was removed from PBS and the membrane edge thereof was contacted with a sheet of absorbent paper to remove excess liquid. The filter membrane was upturned and placed on the surface of the permeabilizing agent, namely the side of the membrane hoop with a code engraved was facing downward close to the fluid, and incubated at room temperature for 5 min.

2. The liquid was removed, 1 ml PBS was added to each well for washing for twice, soaking for 2 min each time. The filter membranes were maintained in PBS until the next experimental operation.

III. Cell Digestion and mRNA Exposure for Hybridization with Probe

1. A digestive enzyme treating solution was prepared with corresponding concentration.

| Reagent composition | Dosage per sample |
| --- | --- |
| Digestive enzyme | 1.25 µl |
| PBS | 48.75 µl |
| Total volume | 50 µl |

2. The digestive enzyme working solution was vortex-mixed evenly, dispensed to a 24-well plate at 50 µl per well.

3. The filter membranes were removed and placed, upturned, on the surface of the digestive enzyme working solution in a 24 well plate, wherein it was ensured that the downward side of the membrane was in sufficient contact with the liquid without bubbles, and stood at room temperature for 1 h.

4. The liquid was removed, washed three times with 1 ml per well of PBS, each time soaking for 2 min. The filter membranes were kept in PBS buffer until the next experimental operation.

IV. Probe Hybridization: Specific Probe Sequence Binding with a Target mRNA Sequence 1. Probe buffer solution, amplification buffer solution, and color-developing buffer solution were preheated with 40° C. water bath for 20 min before use.

2. The probe working solution was prepared as follows:

| Reagent composition | Dosage per sample |
| --- | --- |
| Probe mixture solution | 8 µl |
| Probe mixture solution (preheated at 40° C.) | 42 µl |
| Total volume | 50.0 µl | vortex-mixed evenly, dispensed to a 24-well plate at 50 µl per well.

3. The filter membranes were removed and placed, upturned, on the surface of the probe working solution in a 24 well plate, wherein it was ensured that the downward side of the membrane was in sufficient contact with the liquid without bubbles.

4. Place the lid on the 24-well plate and incubate for 3 hours at 40±1° C.

5. The liquid was removed, washed three times with 1 ml per well of washing solution, each time soaking for 2 min. The filter membranes were kept in the washing solution until the next experimental operation. The soaking time of sample in the washing solution should not exceed 30 min.

V. Amplification Hybridization: Signal Amplification of Target mRNA Sequence

1. The amplification working solution was prepared as follows:

| Reagent composition | Dosage per sample |
| --- | --- |
| Amplification mixture solution | 2 µl |
| Amplification mixture solution (preheated at 40° C.) | 48 µl |
| Total volume | 50.0 µl | vortex-mixed evenly, dispensed to a 24-well plate at 50 µl per well.

2. The filter membranes were removed and placed, upturned, on the surface of the amplification working solution in a 24 well plate, wherein it was ensured that the downward side of the membrane was in sufficient contact with the liquid without bubbles.

3. Place the lid on the 24-well plate and incubate for 30 minutes at 40±1° C.

4. The liquid was removed, washed three times with 1 ml per well of washing solution, each time soaking for 2 min. The filter membranes were kept in the washing solution until the next experimental operation. The soaking time of sample in the washing solution should not exceed 30 min.

VI. Color Developing: Fluorescence-labeled Target Signal

1. The color-developing working solution was prepared as follows:

| Reagent composition | Dosage per sample |
| --- | --- |
| Color-developing mixture solution | 2 µl |
| Color-developing mixture solution (preheated at 40° C.) | 48 µl |
| 总体积 Total volume | 50.0 µl | vortex-mixed evenly in shaded condition, dispensed to a 24-well plate at 50 µl per well.

2. The filter membranes were removed and placed, upturned, on the surface of the color-developing working in a 24 well plate, wherein it was ensured that the downward side of the membrane was in sufficient contact with the liquid without bubbles.

3. Place the lid on the 24-well plate and incubate for 30 minutes at 40±1° C.

4. The liquid was removed, washed three times with 1 ml per well of washing solution, each time soaking for 2 min. The filter membranes were kept in the washing solution until the next experimental operation. The soaking time of sample in the washing solution should not exceed 30 min.

VII. Observation of CTCs by Fluorescence Microscopy

DAPI as a nuclear fluorescence group, which emits blue fluorescence signal, was used as the reference substance of the present disclosure.

1. The filter membrane was placed on the slide with the cell side facing upward, cut along the inner ring of the hoop, added with 10 μl DAPI-containing anti-quencher, and covered with a 18 mm×18 mm coverslip for direct microscopy observation or kept under −20° C.

2. CTC nuclei with atypia were counted with 20× objective lens.

3. A nucleus with atypia was located with 10× objective lens, added with an oil drop, observed with oil immersion lens, and had the results photographed.

4. Then, next nucleus with atypia was located with 10× objective lens, added with an oil drop, observed with oil immersion lens, and had the results photographed.

5. The operation was repeated until all nuclei with atypia were photographed, the number photographed matching the number counted with 20× objective lens.

Channels used in the microscopy are listed below.

Table 7 Excitation wavelength and emission wavelength of the Fluorescent group

| Fluorescent group | Excitation wavelength (Excitation filter) | Emission wavelength (Emission filter) |
| --- | --- | --- |
| DAPI | 330-385 nm | 420 nm |
| Alexa Fluor 488 | 460-495 nm | 510-550 nm |
| Cy3 | 545-580 nm | 610 nm |
| Cy5 | 616-649 nm | 667-751 nm |

VIII. Identification and Analysis of Detection Results.

1. Identification criteria for positive CTCs

A small amount of circulating tumour cells and remaining leukocytes were enriched on a filter membrane. The criteria for identifying circulating tumour cells are as follows (see FIG. 1):

1) having a circulating tumour cell-specific marker and displaying red and/or green fluorescent signal spots in Cy3 and/or Alexa Fluor 488 channels with the use of this kit.

2) not having a leukocyte-specific marker and displaying no fluorescence signal spot in Cy5 channel with the use of this kit.

3) nuclear DAPI staining being positive.

4) the nucleus of circulating tumour cell having a irregular shape, a diameter greater than 10 μm, and a significantly larger size than the filter membrane pore with a diameter of 7 μm. Leukocyte is about the same size as the filter membrane pore.

2. Typing Criteria for Positive CTCs

Figure 2:
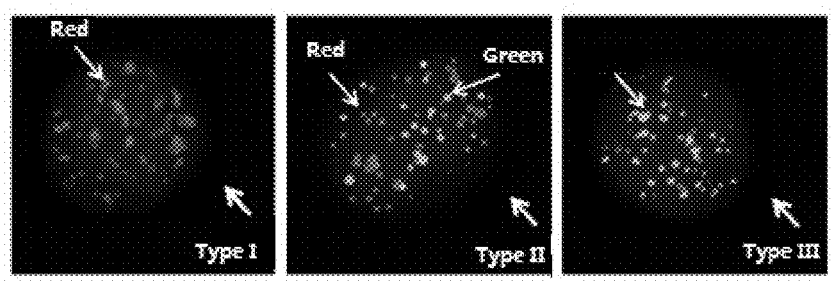
FIG. 2 shows a graph of positive CTC cell typing results in an embodiment of the present disclosure.

This kit utilizes multiple RNA probes specific for multiple CTCs-specific genes. CTCs can be further typed with fluorescent signals of various colors. Type I (the epithelial type) CTCs carry a Cy3 fluorescent group (displaying red fluorescent signal spots), Type III (the mesenchymal type) CTCs carry an Alexa Fluor 488 fluorescent group (displaying green fluorescent signal spots), and Type II (the mixed epithelial-mesenchymal type) CTCs simultaneously express Type I-specific and Type III-specific genes (displaying red and green fluorescent signal spots simultaneously). See FIG. 2. The typing criterias for CTCs are as follows:

TABLE 8

Typing criterias for positive CTCs

| Type | Cy3 | Alexa Fluor 488 | Cy5 | DAPI |
| --- | --- | --- | --- | --- |
| I | + | − | − | + |
| II | + | + | − | + |
| III | − | + | − | + |

3. Peripheral Blood Samples from 20 Tumour Patients were Detected and Observed Using the Aforementioned Detection Method, the Results are Shown Below (Data in the Table Indicate the Cell Numbers):

TABLE 9

Sample detection results

| No. | Epithelial Type | Mixed Epithelial-Mesenchymal Type | Mesenchymal Type | Total CTC |
| --- | --- | --- | --- | --- |
| 1 | 0 | 1 | 0 | 1 |
| 2 | 1 | 2 | 1 | 4 |
| 3 | 0 | 0 | 2 | 2 |
| 4 | 0 | 0 | 7 | 7 |
| 5 | 1 | 5 | 10 | 16 |
| 6 | 0 | 1 | 6 | 7 |
| 7 | 0 | 8 | 4 | 12 |
| 8 | 0 | 4 | 19 | 23 |
| 9 | 0 | 2 | 4 | 6 |
| 10 | 1 | 14 | 15 | 30 |
| 11 | 0 | 1 | 0 | 1 |
| 12 | 0 | 4 | 30 | 34 |
| 13 | 0 | 1 | 4 | 5 |
| 14 | 0 | 7 | 2 | 9 |
| 15 | 1 | 12 | 0 | 13 |
| 16 | 0 | 1 | 0 | 1 |
| 17 | 0 | 5 | 0 | 5 |
| 18 | 0 | 3 | 1 | 4 |
| 19 | 0 | 6 | 12 | 18 |
| 20 | 0 | 17 | 6 | 23 |

EXAMPLE 3

Detection of Cell Lines Using the Kit A According to Example 1

I. Selection of Cell Lines

In the kit of present disclosure, the epithelial cell marker genes are two or more selected from the group consisting of EPCAM, E-cadherin, CEA, KRT5, KRT7, KRT17, and KRT20; the mesenchymal cell marker genes are two or more selected from the group consisting of VIMENTIN, N-cadherin, TWIST1, AKT2, ZEB2, ZEB1, FOXC1, FOXC2, SNAI1, and SNAI2; and the leukocyte marker gene is CD45. The epithelial marker genes, mesenchymal marker genes, and leukocyte marker genes provided in this disclosure are genes selected by the inventors through numerous experiments and statistical analysis that specifically express on CTCs, with good specificity and accuracy for identification and typing of CTCs.

In this example, an epithelial type cell line MCF-10A, a mesenchymal type tumour cell line U118, and a mixed epithelial-mesenchymal type lung cancer cell line PC-9 were used for experiments, while CCRF-HSB-2 lymphocytoblast was used as a negative control. A person skilled in the art will be able to obtain these cell lines commercially as long as the cell line names are provided. About 1000 MCF-10A cells (confirmed with a cytometer) were taken, mixed evenly, and divided into five equal aliquots and numbered as 21-25. About 1000 U118 cells (confirmed with a cytometer) were taken, mixed evenly, and divided into five equal aliquots and numbered as 26-30. About 1000 PC-9 cells (confirmed with a cytometer) were taken, mixed evenly, and divided into five equal aliquots and numbered as 31-35. About 1000 CCRF-HSB-2 cells (confirmed with a cytometer) were taken, mixed evenly, and divided into five equal aliquots and numbered as 36-40.

II. Sample Detection

All the probes in the kit A according to Example 1 (including all the marker genes: the epithelial cell marker genes EPCAM, E-cadherin, CEA, KRT5, KRT7, KRT17, and KRT20; and the mesenchymal cell marker genes VIMENTIN, N-cadherin, TWIST1, AKT2, ZEB2, ZEB1, FOXC1, FOXC2, SNAI1, and SNAI2) and the leukocyte marker gene CD45 were used. Samples 21-40 were tested according to the detection process and method according to Example 2. 50 cells with DAPI blue fluorescent signals in each sample were read, wherein cell numbers in the samples were selected by automatic scanning of a fluorescence microscope. For fluorescent signal intensity of a target detection marker, the number of fluorescent spots of a corresponding color was read for the 50 cells and an average spot number was calculated. The specific detection results are as follows:

TABLE 10

Sample detection results

| No. | Cell line in sample | Cell number in sample | Cell number showing fluorescence | average fluorescent spots | | | Detection rate |
|---|---|---|---|---|---|---|---|
| | | | | Epithelial marker | Mesenchymal marker | Leukocyte marker | |
| 21 | MCF-10A | 50 | 50 | 26 | 0 | 0 | 100% |
| 22 | | 50 | 50 | 26 | 0 | 0 | 100% |
| 23 | | 50 | 50 | 26 | 0 | 0 | 100% |
| 24 | | 50 | 50 | 26 | 0 | 0 | 100% |
| 25 | | 50 | 50 | 26 | 0 | 0 | 100% |
| 26 | U118 | 50 | 50 | 0 | 30 | 0 | 100% |
| 27 | | 50 | 50 | 0 | 30 | 0 | 100% |
| 28 | | 50 | 50 | 0 | 30 | 0 | 100% |
| 29 | | 50 | 50 | 0 | 30 | 0 | 100% |
| 30 | | 50 | 50 | 0 | 30 | 0 | 100% |
| 31 | PC-9 | 50 | 50 | 21 | 28 | 0 | 100% |
| 32 | | 50 | 50 | 21 | 28 | 0 | 100% |
| 33 | | 50 | 50 | 21 | 28 | 0 | 100% |
| 34 | | 50 | 50 | 21 | 28 | 0 | 100% |
| 35 | | 50 | 50 | 21 | 28 | 0 | 100% |
| 36 | CCRF-HSB-2 | 50 | 50 | 0 | 0 | 36 | 100% |
| 37 | | 50 | 50 | 0 | 0 | 36 | 100% |
| 38 | | 50 | 50 | 0 | 0 | 36 | 100% |
| 39 | | 50 | 50 | 0 | 0 | 36 | 100% |
| 40 | | 50 | 50 | 0 | 0 | 36 | 100% |

Comparison of detection results of the four cell lines in the samples demonstrated that the kit disclosed herein can accomplish detection of epithelial, mesenchymal, and leukocyte marker genes with a 100% detection rate for lymphocytoblasts in the cell lines MCF-10A, U118, PC-9, and CCRF-HSB-2 in the samples. Expression of epithelial and/or mesenchymal cell marker genes was only detected in the cell lines MCF-10A, U118, and PC-9, but not in the lymphocytoblasts. Therefore, it indicates that the kit disclosed herein can effectively distinguish tumour cells and leukocytes in a sample. Meanwhile, as demonstrated by the detection results of the epithelial type cell line MCF-10A, the mesenchymal type tumour cell line U118, and the mixed epithelial-mesenchymal type lung cancer cell line PC-9, the ephithelial and mesenchymal marker genes selected for use in the kit disclosed herein can accurately type the cells detected (the epithelial type, mesenchymal type, and mixed epithelial-mesenchymal type), by only detecting the fluorescent signals for ephithelial marker genes in the epithelial type cell lines, only detecting the fluorescent signals for mesenchymal marker genes in the mesenchymal type cell lines, and detecting the fluorescent signals for both ephithelial and mesenchymal marker genes in the mixed epithelial-mesenchymal type cell lines. Therefore, the results indicate good specificity and accuracy of the cell-typing markers selected for use in the kit disclosed herein.

EXAMPLE 4

Selection of Cell Marker Genes of Different Types

I. Design for Preparation of a Kit (Selection of Numbers and Types of Target Detection Marker Genes)

The epithelial cell marker genes of the kit disclosed herein are selected from the group consisting of EPCAM, E-cadherin, CEA, KRT5, KRT7, KRT17, and KRT20, wherein choices were made in accordance with each experimental group; and the mesenchymal cell marker genes are: VIMENTIN, N-cadherin, TWIST1, AKT2, ZEB2, ZEB1, FOXC1, FOXC2, SNAI1, and SNAI2.

See Experimental groups 1-4 for choices of epithelial cell marker genes, wherein one, two, five and seven kinds of marker genes were chosen respectively for comparison of detection results. However, all target genes were used for mesenchymal marker genes and CD45 was used for leukocyte marker gene. The specific designs are shown in Table 11.

The composition, numbers, detection method, and the like, of the capture probes, amplification probes, and labeled probes corresponding to each group of marker genes of this embodiment are described in the kit A of Example 1 as well as in Example 2.

TABLE 11

Selection of epithelial cell marker genes

| Type | Gene types | Experimental group |
|---|---|---|
| Epithelial cell marker gene | EPCAM | 1 |
| | EPCAM、E-cadherin | 2 |
| | EPCAM、E-cadherin、CEA、KRT5、KRT7 | 3 |
| | EPCAM、E-cadherin、CEA、KRT5、KRT7、KRT17、KRT20 | 4 |

II. Sample Detection

In this example, mixed epithelial-mesenchymal type liver cancer cell line HepG2, breast cancer cell line MCF-7, and lung cancer cell line PC-9 were used for experiments. A person skilled in the art will be able to obtain these cell lines commercially as long as the cell line names are provided. About 1000 HepG2 cells (confirmed with a cytometer) were taken, mixed evenly, and divided into five equal aliquots and numbered as 41-45. About 1000 MCF-7 cells (confirmed with a cytometer) were taken, mixed evenly, and divided into five equal aliquots and numbered as 46-50. About 1000 PC-9 cells (confirmed with a cytometer) were taken, mixed evenly, and divided into five equal aliquots and numbered as 51-55.

Samples 41-55 were tested using the kit prepared with marker genes from Table 11 and according to the detection process and method according to Example 2. 50 cells with DAPI blue fluorescent signals in each sample were read, wherein cell numbers in the samples were selected by automatic scanning of a fluorescence microscope. For fluorescent signal intensity of a target detection marker, the number of fluorescent spots of a corresponding color was read for the 50 cells and an average spot number was calculated. The specific detection results are as follows (Data in Table 12 are cell numbers and data in Table 13 are average numbers of fluorescent spots):

TABLE 12

Comparison of detection results using different numbers of epithelial cell marker genes.

| No. | Cell line in sample | Cell number in sample | Experimental group 1 Showing epithelial maker | Experimental group 1 Showing mesenchymal marker | Experimental group 2 Showing epithelial maker | Experimental group 2 Showing mesenchymal marker | Experimental group 3 Showing epithelial maker | Experimental group 3 Showing mesenchymal marker | Experimental group 4 Showing epithelial maker | Experimental group 4 Showing mesenchymal marker |
|---|---|---|---|---|---|---|---|---|---|---|
| 41 | HepG2 | 50 | 48 | 50 | 50 | 50 | 50 | 50 | 50 | 50 |
| 42 | | 50 | 50 | 50 | 50 | 50 | 50 | 50 | 50 | 50 |
| 43 | | 50 | 47 | 50 | 50 | 50 | 50 | 50 | 50 | 50 |
| 44 | | 50 | 49 | 50 | 50 | 50 | 50 | 50 | 50 | 50 |
| 45 | | 50 | 50 | 50 | 50 | 50 | 50 | 50 | 50 | 50 |
| 46 | MCF-7 | 50 | 49 | 50 | 50 | 50 | 50 | 50 | 50 | 50 |
| 47 | | 50 | 50 | 50 | 50 | 50 | 50 | 50 | 50 | 50 |
| 48 | | 50 | 58 | 50 | 50 | 50 | 50 | 50 | 50 | 50 |
| 49 | | 50 | 48 | 50 | 50 | 50 | 50 | 50 | 50 | 50 |
| 50 | | 50 | 49 | 50 | 50 | 50 | 50 | 50 | 50 | 50 |
| 51 | PC-9 | 50 | 50 | 50 | 50 | 50 | 50 | 50 | 50 | 50 |
| 52 | | 50 | 50 | 50 | 50 | 50 | 50 | 50 | 50 | 50 |
| 53 | | 50 | 49 | 50 | 50 | 50 | 50 | 50 | 50 | 50 |
| 54 | | 50 | 50 | 50 | 50 | 50 | 50 | 50 | 50 | 50 |
| 55 | | 50 | 48 | 50 | 50 | 50 | 50 | 50 | 50 | 50 |

TABLE 13

Comparison of average numbers of fluorescent spots using different numbers of epithelial cell marker genes.

| No. | Cell line | Experimental group 1 Red | Experimental group 1 Green | Experimental group 2 Red | Experimental group 2 Green | Experimental group 3 Red | Experimental group 3 Green | Experimental group 4 Red | Experimental group 4 Green |
|---|---|---|---|---|---|---|---|---|---|
| 41 | HepG2 | 9 | 31 | 15 | 31 | 19 | 31 | 25 | 31 |
| 42 | | 9 | 31 | 15 | 31 | 19 | 31 | 25 | 31 |
| 43 | | 9 | 31 | 15 | 31 | 19 | 31 | 25 | 31 |
| 44 | | 9 | 31 | 15 | 31 | 19 | 31 | 25 | 31 |
| 45 | | 9 | 31 | 15 | 31 | 19 | 31 | 25 | 31 |
| 46 | MCF-7 | 7 | 28 | 13 | 28 | 17 | 28 | 21 | 28 |
| 47 | | 7 | 28 | 13 | 28 | 17 | 28 | 21 | 28 |
| 48 | | 7 | 28 | 13 | 28 | 17 | 28 | 21 | 28 |
| 49 | | 7 | 28 | 13 | 28 | 17 | 28 | 21 | 28 |
| 50 | | 7 | 28 | 13 | 28 | 17 | 28 | 21 | 28 |
| 51 | PC-9 | 10 | 26 | 16 | 26 | 20 | 26 | 24 | 26 |
| 52 | | 10 | 26 | 16 | 26 | 20 | 26 | 24 | 26 |

TABLE 13-continued

Comparison of average numbers of fluorescent spots using different numbers of epithelial cell marker genes.

| No. | Cell line | Experimental group 1 | | Experimental group 2 | | Experimental group 3 | | Experimental group 4 | |
|---|---|---|---|---|---|---|---|---|---|
| | | Red | Green | Red | Green | Red | Green | Red | Green |
| 53 | | 10 | 26 | 16 | 26 | 20 | 26 | 24 | 26 |
| 54 | | 10 | 26 | 16 | 26 | 20 | 26 | 24 | 26 |
| 55 | | 10 | 26 | 16 | 26 | 20 | 26 | 24 | 26 |

Comparison of experimental results of Experimental Groups 1-4 demonstrated that, when one, two, five, or seven kinds of epithelial cell marker genes were chosen and all mesenchymal cell marker genes were used, stable detection results for mesenchymal cell marker genes were generated, while variations were seen in detection results for epithelial cell marker genes. Due to the variation in expression of different tumour cell epithelial cell marker genes, detection using only one marker gene results in certain degree of missing detection. Additionally, the detection results stablize when two or more marker genes were used, while the average red fluorescent signal spot gradually increases from Experimental group 1 to 4, as the number of epithelial cell marker gene increases, with improving detection performance. The detection signals were strongest and most stable, with the best performance, when all epithelial cell marker genes were used. Meanwhile, since all 10 mesenchymal cell marker genes were used, stable detection performance was achieved with no variation among the averages of green fluorescent signal spots of the four experimental groups, indicating that increase in the number of epithelial cell marker genes did not affect the detection results of the mesenchymal cell marker genes. Therefore, there is substantially no non-specific binding among the variety of probe types designed for the kit disclosed herein, which yielded a good specificity. The experimental results of gene number selection in mesenchymal cell marker genes are consistent with those of epithelial cell marker genes. Other kits targeted at using different numbers and types of epithelial cell marker genes and mesenchymal cell marker genes also had stable and reliable results, though the specific data thereof are not shown.

EXAMPLE 5

Detection Marker Genes Selected for a Kit

I. Design for Preparation of a Kit (Selection of Numbers and Types of Target Detection Marker Genes)

The epithelial cell marker genes of the kit disclosed herein are selected from the group consisting of EPCAM, E-cadherin, CEA, KRT5, KRT7, KRT17, and KRT20; and the mesenchymal cell marker genes are: VIMENTIN, N-cadherin, TWIST1, AKT2, ZEB2, ZEB1, FOXC1, FOXC2, SNAI1, and SNAI2.

Experimental groups 5-8 were designed by respectively choosing two, four, twelve, and seventeen kinds of marker genes for comparison of the detection results thereof. Marker gene CD45 was used for leukocytes. Specific design is shown in Table 14.

The composition, numbers, detection method, and the like, of the capture probes, amplification probes, and labeled probes corresponding to each group of marker genes of this embodiment are described in the kit A of Example 1 as well as in Example 2.

TABLE 14

Selection of marker genes for a kit

| Epithelial cell marker gene | Mesenchymal cell marker gene | Experimental group |
|---|---|---|
| EPCAM | VIMENTIN | 5 |
| EPCAM、E-cadherin | VIMENTIN、N-cadherin | 6 |
| EPCAM、E-cadherin、CEA、KRT5、KRT7、KRT17 | VIMENTIN、N-cadherin、TWIST1、AKT2、ZEB2、ZEB1 | 7 |
| EPCAM、E-cadherin、CEA、KRT5、KRT7、KRT17、KRT20 | VIMENTIN、N-cadherin、TWIST1、AKT2、ZEB2、ZEB1、FOXC1、FOXC2、SNAI1、SNAI2 | 8 |

II. Sample Detection

In this example, mixed epithelial-mesenchymal type liver cancer cell line HepG2, breast cancer cell line MCF-7, and lung cancer cell line PC-9 were used for experiments. A person skilled in the art will be able to obtain these cell lines commercially as long as the cell line names are provided. About 1000 HepG2 cells (confirmed with a cytometer) were taken, mixed evenly, and divided into five equal aliquots and numbered as 56-60. About 1000 MCF-7 cells (confirmed with a cytometer) were taken, mixed evenly, and divided into five equal aliquots and numbered as 61-65. About 1000 PC-9 cells (confirmed with a cytometer) were taken, mixed evenly, and divided into five equal aliquots and numbered as 66-70.

Samples 56-70 were tested using the kit prepared as described above and following the detection process and method according to Example 2. 50 cells with DAPI blue fluorescent signals in each sample were read, wherein cell numbers in the samples were selected by automatic scanning of a fluorescence microscope. For fluorescent signal intensity of a target detection marker, the number of fluorescent spots of a corresponding color was read for the 50 cells and an average spot number was calculated. The specific detection results are as follows (Data in Table 15 are cell numbers and data in Table 16 are average numbers of fluorescent spots):

TABLE 15

Comparison of detection results using kits with different numbers of marker genes.

| No. | Cell line in sample | Cell number in sample | Experimental group 5 | | Experimental group 6 | | Experimental group 7 | | Experimental group 8 | |
|---|---|---|---|---|---|---|---|---|---|---|
| | | | Showing epithelial maker | Showing mesenchymal marker | Showing epithelial maker | Showing mesenchymal marker | Showing epithelial maker | Showing mesenchymal marker | Showing epithelial maker | Showing mesenchymal marker |
| 56 | HepG2 | 50 | 50 | 48 | 50 | 50 | 50 | 50 | 50 | 50 |
| 57 | | 50 | 49 | 50 | 50 | 50 | 50 | 50 | 50 | 50 |
| 58 | | 50 | 48 | 50 | 50 | 50 | 50 | 50 | 50 | 50 |
| 59 | | 50 | 50 | 49 | 50 | 50 | 50 | 50 | 50 | 50 |
| 60 | | 50 | 49 | 50 | 50 | 50 | 50 | 50 | 50 | 50 |
| 61 | MCF-7 | 50 | 50 | 49 | 50 | 50 | 50 | 50 | 50 | 50 |
| 62 | | 50 | 48 | 50 | 50 | 50 | 50 | 50 | 50 | 50 |
| 63 | | 50 | 50 | 48 | 50 | 50 | 50 | 50 | 50 | 50 |
| 64 | | 50 | 47 | 50 | 50 | 50 | 50 | 50 | 50 | 50 |
| 65 | | 50 | 50 | 47 | 50 | 50 | 50 | 50 | 50 | 50 |
| 66 | PC-9 | 50 | 50 | 50 | 50 | 50 | 50 | 50 | 50 | 50 |
| 67 | | 50 | 58 | 48 | 50 | 50 | 50 | 50 | 50 | 50 |
| 68 | | 50 | 50 | 48 | 50 | 50 | 50 | 50 | 50 | 50 |
| 69 | | 50 | 49 | 48 | 50 | 50 | 50 | 50 | 50 | 50 |
| 70 | | 50 | 48 | 50 | 50 | 50 | 50 | 50 | 50 | 50 |

TABLE 16

Comparison of average numbers of fluorescent spots using kits with different numbers of marker genes.

| No. | Cell line | Experimental group 5 | | Experimental group 6 | | Experimental group 7 | | Experimental group 8 | |
|---|---|---|---|---|---|---|---|---|---|
| | | Red | Green | Red | Green | Red | Green | Red | Green |
| 56 | HepG2 | 7 | 9 | 14 | 15 | 20 | 24 | 23 | 35 |
| 57 | | 7 | 9 | 14 | 15 | 20 | 24 | 23 | 35 |
| 58 | | 7 | 9 | 14 | 15 | 20 | 24 | 23 | 35 |
| 59 | | 7 | 9 | 14 | 15 | 20 | 24 | 23 | 35 |
| 60 | | 7 | 9 | 14 | 15 | 20 | 24 | 23 | 35 |
| 61 | MCF-7 | 9 | 11 | 16 | 17 | 23 | 20 | 26 | 29 |
| 62 | | 9 | 11 | 16 | 17 | 23 | 20 | 26 | 29 |
| 63 | | 9 | 11 | 16 | 17 | 23 | 20 | 26 | 29 |
| 64 | | 9 | 11 | 16 | 17 | 23 | 20 | 26 | 29 |
| 65 | | 9 | 11 | 16 | 17 | 23 | 20 | 26 | 29 |
| 66 | PC-9 | 6 | 9 | 12 | 14 | 18 | 19 | 22 | 31 |
| 67 | | 6 | 9 | 12 | 14 | 18 | 19 | 22 | 31 |
| 68 | | 6 | 9 | 12 | 14 | 18 | 19 | 22 | 31 |
| 69 | | 6 | 9 | 12 | 14 | 18 | 19 | 22 | 31 |
| 70 | | 6 | 9 | 12 | 14 | 18 | 19 | 22 | 31 |

Comparison of experimental results of Experimental Groups 5-8 demonstrated that, when two marker genes were used (Experimental Group 5), false negative results appeared due to varied expression of genes on different cells. The results stablized when four or more than four marker genes were used in detection, while the average red fluorescent signal spot corresponding to the two cell type marker genes on the cells gradually increases from Experimental group 5 to 8, as the number of epithelial cell marker gene increases, with improving detection performance. The detection signals were strongest and most stable, with the best performance, when all cell marker genes were used. Other kits targeted at using different numbers and types also had stable and reliable results, though the specific data thereof are not shown.

EXAMPLE 6

Detection of Circulating Tumour Cell Typing mRNA In Situ Hybridization Using Kits with Different Spacer Arms I. Design for Preparation of a Kit (Selection of Spacer Arms)

The epithelial cell marker genes (7 genes in total) were used for example, empolying different spacer arms respectively. The composition, numbers, detection method, and the like, of the other capture probes, amplification probes, and labeled probes corresponding to each group of marker genes of this embodiment are described in the kit A of Example 1, except for the only difference in their spacer arms, and the detection methods were described in Example 2. Spacer arms are the same in corresponding capture probes and amplification probes.

TABLE 17

Spacer arm and length thereof

| Spacer arm type | Length | Experimental group |
|---|---|---|
| poly (dT) | 5 | 9 |
| poly (dA) | 8 | 10 |
| (CH2) n | 15 | 11 |
| poly (TTG) | 3 | 12 |

II. Sample Detection

In this example, mixed epithelial-mesenchymal type liver cancer cell line HepG2, breast cancer cell line MCF-7, and lung cancer cell line PC-9 were used for experiments. A person skilled in the art will be able to obtain these cell lines commercially as long as the cell line names are provided. About 1000 HepG2 cells (confirmed with a cytometer) were taken, mixed evenly, and divided into five equal aliquots and numbered as 71-75. About 1000 MCF-7 cells (confirmed with a cytometer) were taken, mixed evenly, and divided into five equal aliquots and numbered as 76-80. About 1000 PC-9 cells (confirmed with a cytometer) were taken, mixed evenly, and divided into five equal aliquots and numbered as 81-85.

Samples 71-85 were tested using the kit prepared with marker genes from Table 11 and following the detection process and method according to Example 2. 50 cells with DAPI blue fluorescent signals in each sample were read, wherein cell numbers in the samples were selected by automatic scanning of a fluorescence microscope. The specific detection results are as follows (Data in the table are cell numbers):

marker genes and the specific data thereof are not shown. Other kits targeted at using different spacer sequences in the capture probes, amplification probes, and labeled probes also had stable and reliable results, though the specific data thereof are not shown.

EXAMPLE 7

Application of Labeled Probes

I. Design for Preparation of a Kit (Signal Detection Component)

There are two choices of signal detection components for the kit disclosed herein: 1) a fluorescent group as a 3'-terminal modification in the P4 sequence of the amplification probe; and 2) the P5 sequence of the labeled probe being able to bind to the 3'-terminal P4 sequence of the amplification probe and 3'-terminal fluorescent group being present at the 3' terminal of the labeled probe. Either of the two signal detection components can implement signal amplification and normal signal detection. However, the use of the labeled probe modified with a fluorescent group allows more stable detection signal and better performance.

The two signal detection components for detecting epithelial cell marker genes in the kit disclosed herein are demonstrated as example, the specific designs thereof shown in Table 19. In other words, the kit compositions are:

Experimental group 13: the composition and numbers of capture probes and amplification probes were the same as those of the kit A according to Example 1, except for a fluorescent group Cy3 as a 3'-terminal modification of the amplification probe; and there is no labeled probe.

TABLE 18

Comparison of experimental results using detection probes with different spacer arms for epithelial cell marker genes.

| | | | Experimental group 9 | | Experimental group 10 | | Experimental group 11 | | Experimental group 12 | |
|---|---|---|---|---|---|---|---|---|---|---|
| No. | Cell line in sample | Cell number in sample | Showing epithelial maker | Showing mesenchymal marker | Showing epithelial maker | Showing mesenchymal marker | Showing epithelial maker | Showing mesenchymal marker | Showing epithelial maker | Showing mesenchymal marker |
| 71 | HepG2 | 50 | 50 | 50 | 50 | 50 | 50 | 50 | 50 | 50 |
| 72 | | 50 | 50 | 50 | 50 | 50 | 50 | 50 | 50 | 50 |
| 73 | | 50 | 50 | 50 | 50 | 50 | 50 | 50 | 50 | 50 |
| 74 | | 50 | 50 | 50 | 50 | 50 | 50 | 50 | 50 | 50 |
| 75 | | 50 | 50 | 50 | 50 | 50 | 50 | 50 | 50 | 50 |
| 76 | MCF-7 | 50 | 50 | 50 | 50 | 50 | 50 | 50 | 50 | 50 |
| 77 | | 50 | 50 | 50 | 50 | 50 | 50 | 50 | 50 | 50 |
| 78 | | 50 | 50 | 50 | 50 | 50 | 50 | 50 | 50 | 50 |
| 79 | | 50 | 50 | 50 | 50 | 50 | 50 | 50 | 50 | 50 |
| 80 | | 50 | 50 | 50 | 50 | 50 | 50 | 50 | 50 | 50 |
| 81 | PC-9 | 50 | 50 | 50 | 50 | 50 | 50 | 50 | 50 | 50 |
| 82 | | 50 | 50 | 50 | 50 | 50 | 50 | 50 | 50 | 50 |
| 83 | | 50 | 50 | 50 | 50 | 50 | 50 | 50 | 50 | 50 |
| 84 | | 50 | 50 | 50 | 50 | 50 | 50 | 50 | 50 | 50 |
| 85 | | 50 | 50 | 50 | 50 | 50 | 50 | 50 | 50 | 50 |

Comparison of experimental results of the four experimental groups demonstrated no variation in the detection results among the four experimental designs. Therefore, the four spacer arm designs are equally effective in their performance. The experimental results of detection using different spacer arms in mesenchymal cell and leukocyte marker genes are consistent with those of epithelial cell Experimental group 14: the composition and numbers of capture probes and amplification probes were the same as those of the kit A according to Example 1, and the amplification probe had no fluorescent group, but had a labeled probe with a fluorescent group Cy3 as a 3'-terminal modification in the P5 sequence thereof

TABLE 19

Signal detection component

| Signal detection component | Type | Sequence component (5'-3') | Experimental group |
|---|---|---|---|
| P4-Cy3 | P4 | GTACGTCGTAATTTGAATCTGTAG-Cy3 | Experimental group 13 |
| P4-P5-Cy3 | P4 P5-Cy3 | GTACGTCGTAATTTGAATCTGTAG CTACAGATTCAAATTACGACGTAC-Cy3 | Experimental group 14 |

II. Sample Detection

In this example, mixed epithelial-mesenchymal type liver cancer cell line HepG2, breast cancer cell line MCF-7, and lung cancer cell line PC-9 were used for experiments. A person skilled in the art will be able to obtain these cell lines commercially as long as the cell line names are provided. About 1000 HepG2 cells (confirmed with a cytometer) were taken, mixed evenly, and divided into five equal aliquots and numbered as 86-90. About 1000 MCF-7 cells (confirmed with a cytometer) were taken, mixed evenly, and divided into five equal aliquots and numbered as 91-95. About 1000 PC-9 cells (confirmed with a cytometer) were taken, mixed evenly, and divided into five equal aliquots and numbered as 96-100.

Samples 86-100 were tested using the kit prepared as described above and following the detection process and method according to Example 2. 50 cells with DAPI blue fluorescent signals in each sample were read, wherein cell numbers in the samples were selected by automatic scanning of a fluorescence microscope. For fluorescent signal intensity of a target detection marker, the number of fluorescent spots of a corresponding color was read for the 50 cells and an average spot number was calculated. The specific detection results are as follows (Data in Table 20 are cell numbers and data in Table 21 are average numbers of fluorescent spots):

TABLE 21

Comparison of average numbers of fluorescent spots detection results of epithelial cell marker genes using different signal detection probes.

| | | Experimental group 13 | | Experimental group 14 | |
|---|---|---|---|---|---|
| No. | Cell line | Red | Green | Red | Green |
| 86 | HepG2 | 18 | 30 | 24 | 30 |
| 87 | | 18 | 30 | 24 | 30 |
| 88 | | 18 | 30 | 24 | 30 |
| 89 | | 18 | 30 | 24 | 30 |
| 90 | | 18 | 30 | 24 | 30 |
| 91 | MCF-7 | 15 | 32 | 22 | 32 |
| 92 | | 15 | 32 | 22 | 32 |
| 93 | | 15 | 32 | 22 | 32 |
| 94 | | 15 | 32 | 22 | 32 |
| 95 | | 15 | 32 | 22 | 32 |
| 96 | PC-9 | 13 | 38 | 19 | 38 |
| 97 | | 13 | 38 | 19 | 38 |
| 98 | | 13 | 38 | 19 | 38 |
| 99 | | 13 | 38 | 19 | 38 |
| 100 | | 13 | 38 | 19 | 38 |

The detection results of the two designs were statistically analyzed and demonstrated no variation in the detection results of the cell numbers in the samples between the two experimental designs. Therefore, the two signal detection components are equally effective in their performance. Using the labeled probes modified with a fluorescent group (i.e., Experimental Group 14), more epithelial cell marker gene fluorescence spots were detected, the signals were

TABLE 20

Comparison of detection results of epithelial cell marker genes using different signal detection probes.

| | | | Experimental group 13 | | Experimental group 14 | |
|---|---|---|---|---|---|---|
| No. | Cell line in sample | Cell number in sample | Showing epithelial maker | Showing mesenchymal marker | Showing epithelial maker | Showing mesenchymal marker |
| 86 | HepG2 | 50 | 50 | 50 | 50 | 50 |
| 87 | | 50 | 50 | 50 | 50 | 50 |
| 88 | | 50 | 50 | 50 | 50 | 50 |
| 89 | | 50 | 50 | 50 | 50 | 50 |
| 90 | | 50 | 50 | 50 | 50 | 50 |
| 91 | MCF-7 | 50 | 50 | 50 | 50 | 50 |
| 92 | | 50 | 50 | 50 | 50 | 50 |
| 93 | | 50 | 50 | 50 | 50 | 50 |
| 94 | | 50 | 50 | 50 | 50 | 50 |
| 95 | | 50 | 50 | 50 | 50 | 50 |
| 96 | PC-9 | 50 | 50 | 50 | 50 | 50 |
| 97 | | 50 | 50 | 50 | 50 | 50 |
| 98 | | 50 | 50 | 50 | 50 | 50 |
| 99 | | 50 | 50 | 50 | 50 | 50 |
| 100 | | 50 | 50 | 50 | 50 | 50 | more stable, and the performance thereof was better. The experimental results of detection in mesenchymal cell marker genes are consistent with those of epithelial cell marker genes and the specific data thereof are not shown.

EXAMPLE 8

Selection of Numbers of Capture Probes for Marker Genes

I. Design for Preparation of a Kit (Selection of Numbers of Capture Probes)

The circulating tumour cell typing and identification kit designed 10 capture probes for each marker gene of different cell types, respectively. In addition, the same P2 sequence is used for the capture probes for the marker genes of the same cell type. In use, detection for each target gene can be accomplished with desired specificity and consistency by selecting at least two corresponding capture probes.

To examine the effect of capture probe number selection on the detection performance of the kit, the capture probe number for the epithelial cell marker gene EPCAM was used as an example. See Experimental Groups 15-17, in which 1, 2, and 10 capture probes were chosen, respectively for comparison of the detection results thereof. In this comparative experiment, only EPCAM was used for epithelial cell marker gene, while all genes and probes for the mesenchymal and leukocyte marker genes listed in the kit A according to Example 1 were used.

TABLE 22

Selection of capture probes for epithelial cell marker gene EPCAM

| Number of probes | Capture probe | Experimental group |
|---|---|---|
| 1 | SEQ ID NO. 1 | 15 |
| 2 | SEQ ID NO. 1<br>SEQ ID NO. 2 | 16 |

TABLE 22-continued

Selection of capture probes for epithelial cell marker gene EPCAM

| Number of probes | Capture probe | Experimental group |
|---|---|---|
| 10 | SEQ ID NO. 1<br>SEQ ID NO. 2<br>SEQ ID NO. 3<br>SEQ ID NO. 4<br>SEQ ID NO. 5<br>SEQ ID NO. 6<br>SEQ ID NO. 7<br>SEQ ID NO. 8<br>SEQ ID NO. 9<br>SEQ ID NO. 10 | 17 |

II. Sample Detection

In this example, mixed epithelial-mesenchymal type liver cancer cell line HepG2, breast cancer cell line MCF-7, and lung cancer cell line PC-9 were used for experiments. A person skilled in the art will be able to obtain these cell lines commercially as long as the cell line names are provided. About 1000 HepG2 cells (confirmed with a cytometer) were taken, mixed evenly, and divided into five equal aliquots and numbered as 101-105. About 1000 MCF-7 cells (confirmed with a cytometer) were taken, mixed evenly, and divided into five equal aliquots and numbered as 106-110. About 1000 PC-9 cells (confirmed with a cytometer) were taken, mixed evenly, and divided into five equal aliquots and numbered as 111-115.

Samples 101-115 were tested using the kit prepared as described above and following the detection process and method according to Example 2. 50 cells with DAPI blue fluorescent signals in each sample were read, wherein cell numbers in the samples were selected by automatic scanning of a fluorescence microscope. For fluorescent signal intensity of a target detection marker, the number of fluorescent spots of a corresponding color was read for the 50 cells and an average spot number was calculated. The specific detection results are as follows (Data in Table 23 are cell numbers and data in Table 24 are average numbers of fluorescent spots):

TABLE 23

Comparison of detection results for epithelial cell marker gene EPCAM using different numbers of capture probes.

| No. | Cell linein sample | Cell number in sample | Experimental group 15 | | Experimental group 16 | | Experimental group 17 | |
|---|---|---|---|---|---|---|---|---|
| | | | Showing epithelial maker | Showing mesenchymal marker | Showing epithelial maker | mesenchymal marke | Showing epithelial maker | mesenchymal marke |
| 101 | HepG2 | 50 | 46 | 50 | 48 | 50 | 48 | 50 |
| 102 | | 50 | 46 | 50 | 48 | 50 | 48 | 50 |
| 103 | | 50 | 46 | 50 | 48 | 50 | 48 | 50 |
| 104 | | 50 | 46 | 50 | 48 | 50 | 48 | 50 |
| 105 | | 50 | 46 | 50 | 48 | 50 | 48 | 50 |
| 106 | MCF-7 | 50 | 45 | 50 | 47 | 50 | 47 | 50 |
| 107 | | 50 | 45 | 50 | 47 | 50 | 47 | 50 |
| 108 | | 50 | 45 | 50 | 47 | 50 | 47 | 50 |
| 109 | | 50 | 45 | 50 | 47 | 50 | 47 | 50 |
| 110 | | 50 | 45 | 50 | 47 | 50 | 47 | 50 |
| 111 | PC-9 | 50 | 47 | 50 | 48 | 50 | 48 | 50 |
| 112 | | 50 | 47 | 50 | 48 | 50 | 48 | 50 |
| 113 | | 50 | 47 | 50 | 48 | 50 | 48 | 50 |
| 114 | | 50 | 47 | 50 | 48 | 50 | 48 | 50 |
| 115 | | 50 | 47 | 50 | 48 | 50 | 48 | 50 |

TABLE 24

Comparison of average numbers of fluorescent spots
detection results of epithelial cell marker gene
EPCAM using different signal detection probes.

| No. | Cell line | Experimental group 15 | | Experimental group 16 | | Experimental group 17 | |
|---|---|---|---|---|---|---|---|
| | | Red | Green | Red | Green | Red | Green |
| 101 | HepG2 | 4 | 34 | 7 | 34 | 9 | 34 |
| 102 | | 4 | 34 | 7 | 34 | 9 | 34 |
| 103 | | 4 | 34 | 7 | 34 | 9 | 34 |
| 104 | | 4 | 34 | 7 | 34 | 9 | 34 |
| 105 | | 4 | 34 | 7 | 34 | 9 | 34 |
| 106 | MCF-7 | 6 | 31 | 9 | 31 | 9 | 31 |
| 107 | | 6 | 31 | 9 | 31 | 12 | 31 |
| 108 | | 6 | 31 | 9 | 31 | 12 | 31 |
| 109 | | 6 | 31 | 9 | 31 | 12 | 31 |
| 110 | | 6 | 31 | 9 | 31 | 12 | 31 |
| 111 | PC-9 | 5 | 35 | 8 | 35 | 10 | 35 |
| 112 | | 5 | 35 | 8 | 35 | 10 | 35 |
| 113 | | 5 | 35 | 8 | 35 | 10 | 35 |
| 114 | | 5 | 35 | 8 | 35 | 10 | 35 |
| 115 | | 5 | 35 | 8 | 35 | 10 | 35 |

Comparison of the three experimental groups indicated that, when only epithelial cell marker gene EPCAM was chosen for use, the detection can be finished with 1, 2, or 10 capture probes. When two or more capture probes were used, good specificity and stability were achieved. When all 10 capture probes were used, most fluorescent signal spots were detected for the epithelial genes, the signals were stronger and more stable, and the detection performance was optimized.

Other kits targeted at using different numbers of capture probes for epithelial, mesenchymal, and leukocyte marker genes also had stable and reliable results, though the specific data thereof are not shown.

The technical features of the embodiments described above can be used in any combination as desired. For the purpose of conciseness, not all possible combinations are described herein. However, such combination should all be considered within the scope of the present disclosure provide that there is no contradiction.

The detailed embodiments described herein are only for the purpose of illustrating the present disclosure, and are not intended to limit the scope of the present disclosure in any way. It would be understand by a person skilled in the art that various changes and modifications can be made to the embodiments described herein without departing from the scope and spirit of the present disclosure. Such changes and modifications are contemplated by the present disclosure, the scope of which should only be defined by the following claims.

The invention claimed is:

1. A circulating tumour cell typing and identification kit for detecting marker gene mRNAs comprising;
at least one capture probe for each marker gene mRNA, an amplification probe for each marker gene mRNA; and a labeled probe for each marker gene mRNA,
wherein the marker gene mRNAs comprises at least two epithelial cell marker gene mRNAs and at least two mesenchymal cell marker gene mRNAs,
wherein the at least two epithelial cell marker gene mRNAs comprise EPCAM mRNA and E-cadherin mRNAs and wherein the at least two mesenchymal cell marker gene mRNAs comprise VIMENTIN mRNA and TWIST 1 mRNAs;
wherein each of the capture probe has the following, base composition from 5'-terminal to 3'-terminal in sequence: a specific sequence P1, a spacer arm sequence, and a P2 sequence;
wherein each amplification probe has the following base composition from 5'-terminal to 3'-terminal in sequence: a P3 sequence, a spacer arm sequence, and a P4 sequence;
wherein each labeled probe has a P5 sequence and a fluorescent group as a terminal modification,
wherein different fluorescent groups are used for marker genes of different cell types;
wherein the P1 specific sequence for the EPCAM mRNA is SEQ ID NO: 5 and the P2 sequence for the EPCAM mRNA is SEQ ID NO. 181;
wherein the P1 specific sequence for the E-cadherin mRNA is SEQ ID NO. 16 and the P2 sequence for the E-cadherin mRNA is SEQ ID NO. 181;
wherein the P3 for the epithelial cell marker gene mRNAs is SEQ ID NO. 184 and the P4 sequence is SEQ NO. 187;
wherein the P1 specific sequence for the VIMENTIN mRNA is SEQ ID NO:78 and the P2 sequence for the VIMENTIN mRNA is SEQ ID NO 182;
wherein the P1 specific sequence for TWIST1 mRNA is SEQ ID NO: 95 and the P2 sequence for TWIST1 mRNA is SEQ ID NO: 182; and
wherein the P3 sequence for the mesenchymal cell marker gene mRNAs is SEQ ID NO: 185 and the P4 sequence is SEQ ID NO: 188.

2. The circulating tumour cell typing and identification kit according to claim 1, wherein the marker gene mRNA further comprises leukocyte marker gene mRNA, wherein the leukocyte marker gene mRNA is CD45 mRNA.

3. The circulating tumour cell typing and identification kit according to claim 2, wherein the P1 specific sequences within each capture probe for the CD45 gene is selected from SEQ ID NO: 171-180 and the P2 sequence is SEQ ID NO: 183, and
  wherein the amplification probe for CD45 mRNA comprises the P3 sequence comprising SEQ ID NO: 186 and P4 sequence comprising SEQ ID NO: 189.

4. The circulating tumour cell typing and identification kit according to claim 2, wherein the at least two epithelial cell marker gene mRNAs further comprise CEA, KRT5, KRT7, KRT17, and KRT20 mRNAs, and
  wherein the at least two mesenchymal cell marker gene mRNAs further comprise of N-cadherin, AKT2, ZEB2, ZEB1, FOXC1, FOXC2, SNAI1, and SNAI2 mRNAs.

5. The circulating tumour cell typing and identification kit according to claim 4, wherein,
  the P1 specific sequence within each capture probe for the CEA mRNA is selected from the group consisting of SEQ ID NO.21, SEQ ID NO.22, SEQ ID NO.23, SEQ ID NO.24, SEQ ID NO.25, SEQ ID NO.26, SEQ ID NO.27, SEQ ID NO.28, SEQ ID NO.29, and SEQ ID NO.30, and the P2 sequence within the capture probe for the CEA mRNA is SEQ ID NO.181,
  wherein the P1 specific sequence within each capture probe for the KRT5 mRNA is selected from the group consisting of SEQ ID NO.31, SEQ ID NO.32, SEQ ID NO.33, SEQ ID NO.34, SEQ ID NO.35, SEQ ID NO.36, SEQ ID NO.37, SEQ ID NO.38, SEQ ID NO.39, and SEQ ID NO.40, and the P2 sequence within each capture probe for the KRT5 mRNA is SEQ ID NO.181,
  wherein the P1 specific sequence within each capture probe for the KRT7 mRNA is selected from the group consisting of SEQ ID NO.41, SEQ ID NO.42, SEQ ID NO.43, SEQ ID NO.44, SEQ ID NO.45, SEQ ID NO.46, SEQ ID NO.47, SEQ ID NO.48, SEQ ID NO.49, and SEQ ID NO.50, and the P2 sequence within each capture probe for the KRT7 mRNA is SEQ ID NO.181,
  wherein the P1 specific sequence within each capture probe for the KRT17 mRNA is selected from the group consisting of SEQ ID NO.51, SEQ ID NO.52, SEQ ID NO.53, SEQ ID NO.54, SEQ ID NO.55, SEQ ID NO.56, SEQ ID NO.57, SEQ ID NO.58, SEQ ID NO.59, and SEQ ID NO.60, and the P2 sequence within each capture probe for the KRT17 mRNA is SEQ ID NO.181,
  wherein the P1 specific sequence within each capture probe for the KRT20 mRNA is selected from the group consisting of SEQ ID NO.61, SEQ ID NO.62, SEQ ID NO.63, SEQ ID NO.64, SEQ ID NO.65, SEQ ID NO.66, SEQ ID NO.67, SEQ ID NO.68, SEQ ID NO.69, and SEQ ID NO.70, and the P2 sequence within each capture probe for the KRT20 mRNA is SEQ ID NO.181
  wherein the P1 specific sequence within each capture probe for the N-cadherin mRNA is selected from the group consisting of SEQ ID NO.81, SEQ ID NO.82, SEQ ID NO.83, SEQ ID NO.84, SEQ ID NO.85, SEQ ID NO.86, SEQ ID NO.87, SEQ ID NO.88, SEQ ID NO.89, and SEQ ID NO.90, and the P2 sequence within each capture probe for the N-cadherin mRNA is SEQ ID NO.182,
  the P1 specific sequences for the AKT2 mRNA is selected from the group consisting of SEQ ID NO.101, SEQ ID NO.102, SEQ ID NO.103, SEQ ID NO.104, SEQ ID NO.105, SEQ ID NO.106, SEQ ID NO.107, SEQ ID NO.108, SEQ ID NO.109, and SEQ ID NO.110, and the P2 sequence within each capture probe for the AKT2 mRNA is SEQ ID NO.182,
  the P1 specific sequences for the ZEB2 mRNA is selected from the group consisting of SEQ ID NO.111, SEQ ID NO.112, SEQ ID NO.113, SEQ ID NO.114, SEQ ID NO.115, SEQ ID NO.116, SEQ ID NO.117, SEQ ID NO.118, SEQ ID NO.119, and SEQ ID NO.120, and the P2 sequence within each capture probe for the ZEB2 mRNA is SEQ ID NO.182,
  the P1 specific sequences for the ZEB1 mRNA is selected from the group consisting of SEQ ID NO.121, SEQ ID NO.122, SEQ ID NO.123, SEQ ID NO.124, SEQ ID NO.125, SEQ ID NO.126, SEQ ID NO.127, SEQ ID NO.128, SEQ ID NO.129, and SEQ ID NO.130, and the P2 sequence within each capture probe for the ZEB1 mRNA is SEQ ID NO.182,
  the P1 specific sequences for the FOXC1 mRNA is selected from the group consisting of SEQ ID NO.131, SEQ ID NO.132, SEQ ID NO.133, SEQ ID NO.134, SEQ ID NO.135, SEQ ID NO.136, SEQ ID NO.137, SEQ ID NO.138, SEQ ID NO.139, and SEQ ID NO.140, and the P2 sequence within each capture probe for the FOXC1 mRNA is SEQ ID NO.182,
  the P1 specific sequences for the FOXC2 mRNA is selected from the group consisting of SEQ ID NO.141, SEQ ID NO.142, SEQ ID NO.143, SEQ ID NO.144, SEQ ID NO.145, SEQ ID NO.146, SEQ ID NO.147, SEQ ID NO.148, SEQ ID NO.149, and SEQ ID NO.150, and the P2 sequence within each capture probe for the FOXC2 mRNA is SEQ ID NO.182,
  the P1 specific sequences for the SNAI1 mRNA is selected from the group consisting of SEQ ID NO.151, SEQ ID NO.152, SEQ ID NO.153, SEQ ID NO.154, SEQ ID NO.155, SEQ ID NO.156, SEQ ID NO.157, SEQ ID NO.158, SEQ ID NO.159, and SEQ ID NO.160, and the P2 sequence within each capture probe for the SNAI1 mRNA is SEQ ID NO.182, and
  the P1 specific sequences for the SNAI2 mRNA is selected from the group consisting of SEQ ID NO.161, SEQ ID NO.162, SEQ ID NO.163, SEQ ID NO.164, SEQ ID NO.165, SEQ ID NO.166, SEQ ID NO.167, SEQ ID NO.168, SEQ ID NO.169, and SEQ ID NO.170,and the P2 sequence within each capture probe for the SNAI2 mRNA is SEQ ID NO.182.

6. The circulating tumour cell typing and identification kit according to claim 1, wherein the spacer arm sequence comprises 5-10 thymine.

7. The circulating tumour cell typing and identification kit according to claim 1, wherein the fluorescent group is selected from the group consisting of: FAM, TET, JOE, HEX, Cy3, TAMRA, ROX, Texas Red, LC RED640, Cy5, LC RED705, and Alexa Fluor 488, and wherein different fluorescent groups are used for marker genes of different cell types.

8. The circulating tumour cell typing and identification kit of claim 1, further comprising:
  one or more additional capture probes for the EPCAM mRNA, wherein the P1 specific sequence within each additional capture probe for the EPCAM mRNA is selected from the group consisting of: SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, and SEQ ID NO.10, and the P2 specific sequence within each additional capture probe for the EPCAM mRNA is SEQ ID NO. 181, one or more additional capture probes for the E-cadherin mRNA, wherein the P1 specific sequence within each additional capture probe for the E-cadherin mRNA is selected from the group consisting of: SEQ ID NO.11, SEQ ID NO.12, SEQ ID NO.13, SEQ ID NO.14, SEQ ID NO.15, SEQ ID NO.17, SEQ ID NO.18, SEQ ID NO.19, and SEQ ID NO.20, and the P2 sequence with each additional capture probe for the E-cadherin mRNA is SEQ ID NO.181, one or more additional capture probes for the VIMENTIN mRNA, wherein, the P1 specific sequence within each additional capture probe for the VIMENTIN mRNA is selected from the group consisting of: SEQ ID NO.71, SEQ ID NO.72, SEQ ID NO.73, SEQ ID NO.74, SEQ ID NO.75, SEQ ID NO.76, SEQ ID NO.77, SEQ ID NO.79, and SEQ ID NO.80, and the P2 sequence within each additional capture probe for the VIMENTIN mRNA is SEQ ID NO. 182, and one or more additional capture probes for the TWIST1 mRNA, wherein the P1 specific sequence within each additional capture probe for the TWIST1 mRNA is selected from the group consisting of: SEQ ID NO.91, SEQ ID NO.92, SEQ ID NO.93, SEQ ID NO.94, SEQ ID NO.96, SEQ ID NO.97, SEQ ID NO.98, SEQ ID NO.99, and SEQ ID NO.100, and the P2 sequence within each additional capture probe for the TWIST1 mRNA is SEQ ID NO.182.

\* \* \* \* \*

SEQUENCE LISTING

```
<160> NUMBER OF SEQ ID NOS: 192

<210> SEQ ID NO 1
<211> LENGTH: 20
<212> TYPE: DNA
<213> ORGANISM: Artificial Sequence
<220> FEATURE:
<223> OTHER INFORMATION: Probe

<400> SEQUENCE: 1
ctctcatcgc agtcaggatc                                                     20

<210> SEQ ID NO 2
<211> LENGTH: 20
<212> TYPE: DNA
<213> ORGANISM: Artificial Sequence
<220> FEATURE:
<223> OTHER INFORMATION: Probe

<400> SEQUENCE: 2
acacattctt cctgagctgc                                                     20

<210> SEQ ID NO 3
<211> LENGTH: 20
<212> TYPE: DNA
<213> ORGANISM: Artificial Sequence
<220> FEATURE:
<223> OTHER INFORMATION: Probe

<400> SEQUENCE: 3
agccattcat ttctgccttc                                                     20

<210> SEQ ID NO 4
<211> LENGTH: 20
<212> TYPE: DNA
<213> ORGANISM: Artificial Sequence
<220> FEATURE:
<223> OTHER INFORMATION: Probe
```

```
<400> SEQUENCE: 4
tgatccagta ggttctcact                                               20

<210> SEQ ID NO 5
<211> LENGTH: 20
<212> TYPE: DNA
<213> ORGANISM: Artificial Sequence
<220> FEATURE:
<223> OTHER INFORMATION: Probe

<400> SEQUENCE: 5
cagttgataa cgcgttgtga                                               20

<210> SEQ ID NO 6
<211> LENGTH: 20
<212> TYPE: DNA
<213> ORGANISM: Artificial Sequence
<220> FEATURE:
<223> OTHER INFORMATION: Probe

<400> SEQUENCE: 6
aataagccac atcagctatg                                               20

<210> SEQ ID NO 7
<211> LENGTH: 20
<212> TYPE: DNA
<213> ORGANISM: Artificial Sequence
<220> FEATURE:
<223> OTHER INFORMATION: Probe

<400> SEQUENCE: 7
tgaccaggat ccagatccag                                               20

<210> SEQ ID NO 8
<211> LENGTH: 20
<212> TYPE: DNA
<213> ORGANISM: Artificial Sequence
<220> FEATURE:
<223> OTHER INFORMATION: Probe

<400> SEQUENCE: 8
gccattctct tctttctgga                                               20

<210> SEQ ID NO 9
<211> LENGTH: 20
<212> TYPE: DNA
<213> ORGANISM: Artificial Sequence
<220> FEATURE:
<223> OTHER INFORMATION: Probe

<400> SEQUENCE: 9
catttgtaat ttgtgtccat                                               20

<210> SEQ ID NO 10
<211> LENGTH: 20
<212> TYPE: DNA
<213> ORGANISM: Artificial Sequence
<220> FEATURE:
<223> OTHER INFORMATION: Probe

<400> SEQUENCE: 10
cactattaca aatatatgat                                               20

<210> SEQ ID NO 11
<211> LENGTH: 20
```

```
<212> TYPE: DNA
<213> ORGANISM: Artificial Sequence
<220> FEATURE:
<223> OTHER INFORMATION: Probe

<400> SEQUENCE: 11
cttctgaggc caggagagga                                                  20

<210> SEQ ID NO 12
<211> LENGTH: 20
<212> TYPE: DNA
<213> ORGANISM: Artificial Sequence
<220> FEATURE:
<223> OTHER INFORMATION: Probe

<400> SEQUENCE: 12
cttctttgtc tttgttggat                                                  20

<210> SEQ ID NO 13
<211> LENGTH: 20
<212> TYPE: DNA
<213> ORGANISM: Artificial Sequence
<220> FEATURE:
<223> OTHER INFORMATION: Probe

<400> SEQUENCE: 13
tctctatcca gaggctctgt                                                  20

<210> SEQ ID NO 14
<211> LENGTH: 20
<212> TYPE: DNA
<213> ORGANISM: Artificial Sequence
<220> FEATURE:
<223> OTHER INFORMATION: Probe

<400> SEQUENCE: 14
tccattggat cctcaactgc                                                  20

<210> SEQ ID NO 15
<211> LENGTH: 20
<212> TYPE: DNA
<213> ORGANISM: Artificial Sequence
<220> FEATURE:
<223> OTHER INFORMATION: Probe

<400> SEQUENCE: 15
gtaggtgttc acatcatcgt                                                  20

<210> SEQ ID NO 16
<211> LENGTH: 20
<212> TYPE: DNA
<213> ORGANISM: Artificial Sequence
<220> FEATURE:
<223> OTHER INFORMATION: Probe

<400> SEQUENCE: 16
ccaccagggt atacgtaggg                                                  20

<210> SEQ ID NO 17
<211> LENGTH: 20
<212> TYPE: DNA
<213> ORGANISM: Artificial Sequence
<220> FEATURE:
<223> OTHER INFORMATION: Probe

<400> SEQUENCE: 17
```
ctcgttctca ggcacctgac                                         20

<210> SEQ ID NO 18
<211> LENGTH: 20
<212> TYPE: DNA
<213> ORGANISM: Artificial Sequence
<220> FEATURE:
<223> OTHER INFORMATION: Probe

<400> SEQUENCE: 18
gtatgaacag ctgtgaggat                                         20

<210> SEQ ID NO 19
<211> LENGTH: 20
<212> TYPE: DNA
<213> ORGANISM: Artificial Sequence
<220> FEATURE:
<223> OTHER INFORMATION: Probe

<400> SEQUENCE: 19
tcattcacat ccagcacatc                                         20

<210> SEQ ID NO 20
<211> LENGTH: 20
<212> TYPE: DNA
<213> ORGANISM: Artificial Sequence
<220> FEATURE:
<223> OTHER INFORMATION: Probe

<400> SEQUENCE: 20
tccggattaa tctccagcca                                         20

<210> SEQ ID NO 21
<211> LENGTH: 20
<212> TYPE: DNA
<213> ORGANISM: Artificial Sequence
<220> FEATURE:
<223> OTHER INFORMATION: Probe

<400> SEQUENCE: 21
gtgtcattct ggatgatgtt                                         20

<210> SEQ ID NO 22
<211> LENGTH: 20
<212> TYPE: DNA
<213> ORGANISM: Artificial Sequence
<220> FEATURE:
<223> OTHER INFORMATION: Probe

<400> SEQUENCE: 22
gtatacccgg aactggccag                                         20

<210> SEQ ID NO 23
<211> LENGTH: 20
<212> TYPE: DNA
<213> ORGANISM: Artificial Sequence
<220> FEATURE:
<223> OTHER INFORMATION: Probe

<400> SEQUENCE: 23
ctgattgttt acccaccaca                                         20

<210> SEQ ID NO 24
<211> LENGTH: 20
<212> TYPE: DNA
<213> ORGANISM: Artificial Sequence

```
<220> FEATURE:
<223> OTHER INFORMATION: Probe

<400> SEQUENCE: 24
agaggacatt caggatgact                                              20

<210> SEQ ID NO 25
<211> LENGTH: 20
<212> TYPE: DNA
<213> ORGANISM: Artificial Sequence
<220> FEATURE:
<223> OTHER INFORMATION: Probe

<400> SEQUENCE: 25
agtcccattg acaaaccaag                                              20

<210> SEQ ID NO 26
<211> LENGTH: 20
<212> TYPE: DNA
<213> ORGANISM: Artificial Sequence
<220> FEATURE:
<223> OTHER INFORMATION: Probe

<400> SEQUENCE: 26
ggccagtgtc tgagttatgg                                              20

<210> SEQ ID NO 27
<211> LENGTH: 20
<212> TYPE: DNA
<213> ORGANISM: Artificial Sequence
<220> FEATURE:
<223> OTHER INFORMATION: Probe

<400> SEQUENCE: 27
gctctgcata gactgtgatc                                              20

<210> SEQ ID NO 28
<211> LENGTH: 20
<212> TYPE: DNA
<213> ORGANISM: Artificial Sequence
<220> FEATURE:
<223> OTHER INFORMATION: Probe

<400> SEQUENCE: 28
catagggtcc tacatcattc                                              20

<210> SEQ ID NO 29
<211> LENGTH: 20
<212> TYPE: DNA
<213> ORGANISM: Artificial Sequence
<220> FEATURE:
<223> OTHER INFORMATION: Probe

<400> SEQUENCE: 29
gtgatgttgg agataaagag                                              20

<210> SEQ ID NO 30
<211> LENGTH: 20
<212> TYPE: DNA
<213> ORGANISM: Artificial Sequence
<220> FEATURE:
<223> OTHER INFORMATION: Probe

<400> SEQUENCE: 30
ggttgtgttc tgagcctcag                                              20
```

<210> SEQ ID NO 31
<211> LENGTH: 20
<212> TYPE: DNA
<213> ORGANISM: Artificial Sequence
<220> FEATURE:
<223> OTHER INFORMATION: Probe

<400> SEQUENCE: 31
aagcacccgc aaggctgacc                                               20

<210> SEQ ID NO 32
<211> LENGTH: 20
<212> TYPE: DNA
<213> ORGANISM: Artificial Sequence
<220> FEATURE:
<223> OTHER INFORMATION: Probe

<400> SEQUENCE: 32
ccacctccaa agccatagcc                                               20

<210> SEQ ID NO 33
<211> LENGTH: 20
<212> TYPE: DNA
<213> ORGANISM: Artificial Sequence
<220> FEATURE:
<223> OTHER INFORMATION: Probe

<400> SEQUENCE: 33
caggttctgc ctcacagtct                                               20

<210> SEQ ID NO 34
<211> LENGTH: 20
<212> TYPE: DNA
<213> ORGANISM: Artificial Sequence
<220> FEATURE:
<223> OTHER INFORMATION: Probe

<400> SEQUENCE: 34
aagccagggc caccgaagcc                                               20

<210> SEQ ID NO 35
<211> LENGTH: 20
<212> TYPE: DNA
<213> ORGANISM: Artificial Sequence
<220> FEATURE:
<223> OTHER INFORMATION: Probe

<400> SEQUENCE: 35
ggtcctcacc ctctggatgc                                               20

<210> SEQ ID NO 36
<211> LENGTH: 20
<212> TYPE: DNA
<213> ORGANISM: Artificial Sequence
<220> FEATURE:
<223> OTHER INFORMATION: Probe

<400> SEQUENCE: 36
ttgttctgct gctccaggaa                                               20

<210> SEQ ID NO 37
<211> LENGTH: 20
<212> TYPE: DNA
<213> ORGANISM: Artificial Sequence
<220> FEATURE:
<223> OTHER INFORMATION: Probe -continued

<400> SEQUENCE: 37
tgtcaatctc ggctctcagc                                               20

<210> SEQ ID NO 38
<211> LENGTH: 20
<212> TYPE: DNA
<213> ORGANISM: Artificial Sequence
<220> FEATURE:
<223> OTHER INFORMATION: Probe

<400> SEQUENCE: 38
catgtaggca gcatctacat                                               20

<210> SEQ ID NO 39
<211> LENGTH: 20
<212> TYPE: DNA
<213> ORGANISM: Artificial Sequence
<220> FEATURE:
<223> OTHER INFORMATION: Probe

<400> SEQUENCE: 39
ttgtccatgg agaggaccac                                               20

<210> SEQ ID NO 40
<211> LENGTH: 20
<212> TYPE: DNA
<213> ORGANISM: Artificial Sequence
<220> FEATURE:
<223> OTHER INFORMATION: Probe

<400> SEQUENCE: 40
ctcagcgatg atgctatcca                                               20

<210> SEQ ID NO 41
<211> LENGTH: 20
<212> TYPE: DNA
<213> ORGANISM: Artificial Sequence
<220> FEATURE:
<223> OTHER INFORMATION: Probe

<400> SEQUENCE: 41
cttgtcgatg aaggaggcaa                                               20

<210> SEQ ID NO 42
<211> LENGTH: 20
<212> TYPE: DNA
<213> ORGANISM: Artificial Sequence
<220> FEATURE:
<223> OTHER INFORMATION: Probe

<400> SEQUENCE: 42
cctgcagtgc ctcaagctga                                               20

<210> SEQ ID NO 43
<211> LENGTH: 20
<212> TYPE: DNA
<213> ORGANISM: Artificial Sequence
<220> FEATURE:
<223> OTHER INFORMATION: Probe

<400> SEQUENCE: 43
cttcgtactt attcttgaag                                               20

<210> SEQ ID NO 44

<211> LENGTH: 20
<212> TYPE: DNA
<213> ORGANISM: Artificial Sequence
<220> FEATURE:
<223> OTHER INFORMATION: Probe

<400> SEQUENCE: 44
ccttgctcat gtaggcagca                                          20

<210> SEQ ID NO 45
<211> LENGTH: 20
<212> TYPE: DNA
<213> ORGANISM: Artificial Sequence
<220> FEATURE:
<223> OTHER INFORMATION: Probe

<400> SEQUENCE: 45
aggaagttga tctcatcatt                                          20

<210> SEQ ID NO 46
<211> LENGTH: 20
<212> TYPE: DNA
<213> ORGANISM: Artificial Sequence
<220> FEATURE:
<223> OTHER INFORMATION: Probe

<400> SEQUENCE: 46
ctgcagctct gtcaactccg                                          20

<210> SEQ ID NO 47
<211> LENGTH: 20
<212> TYPE: DNA
<213> ORGANISM: Artificial Sequence
<220> FEATURE:
<223> OTHER INFORMATION: Probe

<400> SEQUENCE: 47
gcagtccttt aggcacctgt                                          20

<210> SEQ ID NO 48
<211> LENGTH: 20
<212> TYPE: DNA
<213> ORGANISM: Artificial Sequence
<220> FEATURE:
<223> OTHER INFORMATION: Probe

<400> SEQUENCE: 48
tccgggtatt ccggaggtcg                                          20

<210> SEQ ID NO 49
<211> LENGTH: 20
<212> TYPE: DNA
<213> ORGANISM: Artificial Sequence
<220> FEATURE:
<223> OTHER INFORMATION: Probe

<400> SEQUENCE: 49
tcgatgtcca gggccagctt                                          20

<210> SEQ ID NO 50
<211> LENGTH: 20
<212> TYPE: DNA
<213> ORGANISM: Artificial Sequence
<220> FEATURE:
<223> OTHER INFORMATION: Probe

<400> SEQUENCE: 50
gccgtgccat atcctgcttg                                            20

<210> SEQ ID NO 51
<211> LENGTH: 20
<212> TYPE: DNA
<213> ORGANISM: Artificial Sequence
<220> FEATURE:
<223> OTHER INFORMATION: Probe

<400> SEQUENCE: 51
tactgagtca ggtgggcatc                                            20

<210> SEQ ID NO 52
<211> LENGTH: 20
<212> TYPE: DNA
<213> ORGANISM: Artificial Sequence
<220> FEATURE:
<223> OTHER INFORMATION: Probe

<400> SEQUENCE: 52
tgctgctcca tctcgcagcg                                            20

<210> SEQ ID NO 53
<211> LENGTH: 20
<212> TYPE: DNA
<213> ORGANISM: Artificial Sequence
<220> FEATURE:
<223> OTHER INFORMATION: Probe

<400> SEQUENCE: 53
tgctttcatg ctgagctggg                                            20

<210> SEQ ID NO 54
<211> LENGTH: 20
<212> TYPE: DNA
<213> ORGANISM: Artificial Sequence
<220> FEATURE:
<223> OTHER INFORMATION: Probe

<400> SEQUENCE: 54
ccagctcact gttggtggcc                                            20

<210> SEQ ID NO 55
<211> LENGTH: 20
<212> TYPE: DNA
<213> ORGANISM: Artificial Sequence
<220> FEATURE:
<223> OTHER INFORMATION: Probe

<400> SEQUENCE: 55
atcttctcat actggtcacg                                            20

<210> SEQ ID NO 56
<211> LENGTH: 20
<212> TYPE: DNA
<213> ORGANISM: Artificial Sequence
<220> FEATURE:
<223> OTHER INFORMATION: Probe

<400> SEQUENCE: 56
acattgatct caccacccac                                            20

<210> SEQ ID NO 57
<211> LENGTH: 20
<212> TYPE: DNA

```
<213> ORGANISM: Artificial Sequence
<220> FEATURE:
<223> OTHER INFORMATION: Probe

<400> SEQUENCE: 57
gccagggtca gctcatccag                                               20

<210> SEQ ID NO 58
<211> LENGTH: 20
<212> TYPE: DNA
<213> ORGANISM: Artificial Sequence
<220> FEATURE:
<223> OTHER INFORMATION: Probe

<400> SEQUENCE: 58
actcaggcgc agggcctgct                                               20

<210> SEQ ID NO 59
<211> LENGTH: 20
<212> TYPE: DNA
<213> ORGANISM: Artificial Sequence
<220> FEATURE:
<223> OTHER INFORMATION: Probe

<400> SEQUENCE: 59
tcctcaattg tcctgtagta                                               20

<210> SEQ ID NO 60
<211> LENGTH: 20
<212> TYPE: DNA
<213> ORGANISM: Artificial Sequence
<220> FEATURE:
<223> OTHER INFORMATION: Probe

<400> SEQUENCE: 60
agctgtagca gctggagtag                                               20

<210> SEQ ID NO 61
<211> LENGTH: 20
<212> TYPE: DNA
<213> ORGANISM: Artificial Sequence
<220> FEATURE:
<223> OTHER INFORMATION: Probe

<400> SEQUENCE: 61
caggcaattt gcagctcctc                                               20

<210> SEQ ID NO 62
<211> LENGTH: 20
<212> TYPE: DNA
<213> ORGANISM: Artificial Sequence
<220> FEATURE:
<223> OTHER INFORMATION: Probe

<400> SEQUENCE: 62
gctgatttct tgcagggagc                                               20

<210> SEQ ID NO 63
<211> LENGTH: 20
<212> TYPE: DNA
<213> ORGANISM: Artificial Sequence
<220> FEATURE:
<223> OTHER INFORMATION: Probe

<400> SEQUENCE: 63
atgacacgac cttgccatcc                                               20
```

```
<210> SEQ ID NO 64
<211> LENGTH: 20
<212> TYPE: DNA
<213> ORGANISM: Artificial Sequence
<220> FEATURE:
<223> OTHER INFORMATION: Probe

<400> SEQUENCE: 64
ttctccttcc agaaggcggc                                                      20

<210> SEQ ID NO 65
<211> LENGTH: 20
<212> TYPE: DNA
<213> ORGANISM: Artificial Sequence
<220> FEATURE:
<223> OTHER INFORMATION: Probe

<400> SEQUENCE: 65
gaaggatatg gtattcgttg                                                      20

<210> SEQ ID NO 66
<211> LENGTH: 20
<212> TYPE: DNA
<213> ORGANISM: Artificial Sequence
<220> FEATURE:
<223> OTHER INFORMATION: Probe

<400> SEQUENCE: 66
actggaggtt ggctaactgg                                                      20

<210> SEQ ID NO 67
<211> LENGTH: 20
<212> TYPE: DNA
<213> ORGANISM: Artificial Sequence
<220> FEATURE:
<223> OTHER INFORMATION: Probe

<400> SEQUENCE: 67
gtctcagctc cgttagttga                                                      20

<210> SEQ ID NO 68
<211> LENGTH: 20
<212> TYPE: DNA
<213> ORGANISM: Artificial Sequence
<220> FEATURE:
<223> OTHER INFORMATION: Probe

<400> SEQUENCE: 68
aaggttcttc tgggccatga                                                      20

<210> SEQ ID NO 69
<211> LENGTH: 20
<212> TYPE: DNA
<213> ORGANISM: Artificial Sequence
<220> FEATURE:
<223> OTHER INFORMATION: Probe

<400> SEQUENCE: 69
taggccatcg acttcctcct                                                      20

<210> SEQ ID NO 70
<211> LENGTH: 20
<212> TYPE: DNA
<213> ORGANISM: Artificial Sequence
<220> FEATURE:
```

<223> OTHER INFORMATION: Probe

<400> SEQUENCE: 70
ttcaggcctt ggagatcagc                                               20

<210> SEQ ID NO 71
<211> LENGTH: 20
<212> TYPE: DNA
<213> ORGANISM: Artificial Sequence
<220> FEATURE:
<223> OTHER INFORMATION: Probe

<400> SEQUENCE: 71
cagaggagcg cgtggcatac                                               20

<210> SEQ ID NO 72
<211> LENGTH: 20
<212> TYPE: DNA
<213> ORGANISM: Artificial Sequence
<220> FEATURE:
<223> OTHER INFORMATION: Probe

<400> SEQUENCE: 72
caccgagtcc tgcaggagcc                                               20

<210> SEQ ID NO 73
<211> LENGTH: 20
<212> TYPE: DNA
<213> ORGANISM: Artificial Sequence
<220> FEATURE:
<223> OTHER INFORMATION: Probe

<400> SEQUENCE: 73
gttggcgaag cggtcattca                                               20

<210> SEQ ID NO 74
<211> LENGTH: 20
<212> TYPE: DNA
<213> ORGANISM: Artificial Sequence
<220> FEATURE:
<223> OTHER INFORMATION: Probe

<400> SEQUENCE: 74
aggatcttat tctgctgctc                                               20

<210> SEQ ID NO 75
<211> LENGTH: 20
<212> TYPE: DNA
<213> ORGANISM: Artificial Sequence
<220> FEATURE:
<223> OTHER INFORMATION: Probe

<400> SEQUENCE: 75
ggtccacctg ccggcgcagc                                               20

<210> SEQ ID NO 76
<211> LENGTH: 20
<212> TYPE: DNA
<213> ORGANISM: Artificial Sequence
<220> FEATURE:
<223> OTHER INFORMATION: Probe

<400> SEQUENCE: 76
tgtcgcgctc cacctcgacg                                               20

```
<210> SEQ ID NO 77
<211> LENGTH: 20
<212> TYPE: DNA
<213> ORGANISM: Artificial Sequence
<220> FEATURE:
<223> OTHER INFORMATION: Probe

<400> SEQUENCE: 77
gcaggcggcc aatagtgtct                                               20

<210> SEQ ID NO 78
<211> LENGTH: 20
<212> TYPE: DNA
<213> ORGANISM: Artificial Sequence
<220> FEATURE:
<223> OTHER INFORMATION: Probe

<400> SEQUENCE: 78
gattccactt tgcgttcaag                                               20

<210> SEQ ID NO 79
<211> LENGTH: 20
<212> TYPE: DNA
<213> ORGANISM: Artificial Sequence
<220> FEATURE:
<223> OTHER INFORMATION: Probe

<400> SEQUENCE: 79
agccacactt tcatattgct                                               20

<210> SEQ ID NO 80
<211> LENGTH: 20
<212> TYPE: DNA
<213> ORGANISM: Artificial Sequence
<220> FEATURE:
<223> OTHER INFORMATION: Probe

<400> SEQUENCE: 80
caaacttgga tttgtaccat                                               20

<210> SEQ ID NO 81
<211> LENGTH: 20
<212> TYPE: DNA
<213> ORGANISM: Artificial Sequence
<220> FEATURE:
<223> OTHER INFORMATION: Probe

<400> SEQUENCE: 81
cctggtgtaa gaactcaggt                                               20

<210> SEQ ID NO 82
<211> LENGTH: 20
<212> TYPE: DNA
<213> ORGANISM: Artificial Sequence
<220> FEATURE:
<223> OTHER INFORMATION: Probe

<400> SEQUENCE: 82
cggtcatcac atatgttcca                                               20

<210> SEQ ID NO 83
<211> LENGTH: 20
<212> TYPE: DNA
<213> ORGANISM: Artificial Sequence
<220> FEATURE:
<223> OTHER INFORMATION: Probe
```

<400> SEQUENCE: 83
gctgccactg tgatgatgtc  20

<210> SEQ ID NO 84
<211> LENGTH: 20
<212> TYPE: DNA
<213> ORGANISM: Artificial Sequence
<220> FEATURE:
<223> OTHER INFORMATION: Probe

<400> SEQUENCE: 84
ggaggattgt cattgacatc  20

<210> SEQ ID NO 85
<211> LENGTH: 20
<212> TYPE: DNA
<213> ORGANISM: Artificial Sequence
<220> FEATURE:
<223> OTHER INFORMATION: Probe

<400> SEQUENCE: 85
tgatccttat cggtcacagt  20

<210> SEQ ID NO 86
<211> LENGTH: 20
<212> TYPE: DNA
<213> ORGANISM: Artificial Sequence
<220> FEATURE:
<223> OTHER INFORMATION: Probe

<400> SEQUENCE: 86
attcccttgg ctaatggcac  20

<210> SEQ ID NO 87
<211> LENGTH: 20
<212> TYPE: DNA
<213> ORGANISM: Artificial Sequence
<220> FEATURE:
<223> OTHER INFORMATION: Probe

<400> SEQUENCE: 87
tggcgaatga tcttaggatt  20

<210> SEQ ID NO 88
<211> LENGTH: 20
<212> TYPE: DNA
<213> ORGANISM: Artificial Sequence
<220> FEATURE:
<223> OTHER INFORMATION: Probe

<400> SEQUENCE: 88
cattaagccg agtgatggtc  20

<210> SEQ ID NO 89
<211> LENGTH: 20
<212> TYPE: DNA
<213> ORGANISM: Artificial Sequence
<220> FEATURE:
<223> OTHER INFORMATION: Probe

<400> SEQUENCE: 89
tcctgtccac atctgtgcag  20

<210> SEQ ID NO 90
<211> LENGTH: 20

```
<212> TYPE: DNA
<213> ORGANISM: Artificial Sequence
<220> FEATURE:
<223> OTHER INFORMATION: Probe

<400> SEQUENCE: 90
gagcaggatg gcaatgatgg                                                    20

<210> SEQ ID NO 91
<211> LENGTH: 19
<212> TYPE: DNA
<213> ORGANISM: Artificial Sequence
<220> FEATURE:
<223> OTHER INFORMATION: Probe

<400> SEQUENCE: 91
gtagctgagc cgctcgtga                                                     19

<210> SEQ ID NO 92
<211> LENGTH: 19
<212> TYPE: DNA
<213> ORGANISM: Artificial Sequence
<220> FEATURE:
<223> OTHER INFORMATION: Probe

<400> SEQUENCE: 92
tggagtccag ctcgtcgct                                                     19

<210> SEQ ID NO 93
<211> LENGTH: 19
<212> TYPE: DNA
<213> ORGANISM: Artificial Sequence
<220> FEATURE:
<223> OTHER INFORMATION: Probe

<400> SEQUENCE: 93
ctgaatcttg ctcagcttg                                                     19

<210> SEQ ID NO 94
<211> LENGTH: 19
<212> TYPE: DNA
<213> ORGANISM: Artificial Sequence
<220> FEATURE:
<223> OTHER INFORMATION: Probe

<400> SEQUENCE: 94
gagggcagcg tggggatga                                                     19

<210> SEQ ID NO 95
<211> LENGTH: 19
<212> TYPE: DNA
<213> ORGANISM: Artificial Sequence
<220> FEATURE:
<223> OTHER INFORMATION: Probe

<400> SEQUENCE: 95
acgcctcgtt cagcgactg                                                     19

<210> SEQ ID NO 96
<211> LENGTH: 19
<212> TYPE: DNA
<213> ORGANISM: Artificial Sequence
<220> FEATURE:
<223> OTHER INFORMATION: Probe

<400> SEQUENCE: 96
```
tgcgctggcg ctcccgcac                                                    19

<210> SEQ ID NO 97
<211> LENGTH: 19
<212> TYPE: DNA
<213> ORGANISM: Artificial Sequence
<220> FEATURE:
<223> OTHER INFORMATION: Probe

<400> SEQUENCE: 97
gctgcgtctg cagctcctc                                                    19

<210> SEQ ID NO 98
<211> LENGTH: 19
<212> TYPE: DNA
<213> ORGANISM: Artificial Sequence
<220> FEATURE:
<223> OTHER INFORMATION: Probe

<400> SEQUENCE: 98
agacttctat cagaatgca                                                    19

<210> SEQ ID NO 99
<211> LENGTH: 19
<212> TYPE: DNA
<213> ORGANISM: Artificial Sequence
<220> FEATURE:
<223> OTHER INFORMATION: Probe

<400> SEQUENCE: 99
agttatccag ctccagagt                                                    19

<210> SEQ ID NO 100
<211> LENGTH: 19
<212> TYPE: DNA
<213> ORGANISM: Artificial Sequence
<220> FEATURE:
<223> OTHER INFORMATION: Probe

<400> SEQUENCE: 100
ttctctggaa acaatgaca                                                    19

<210> SEQ ID NO 101
<211> LENGTH: 20
<212> TYPE: DNA
<213> ORGANISM: Artificial Sequence
<220> FEATURE:
<223> OTHER INFORMATION: Probe

<400> SEQUENCE: 101
gcaggcagcg tatgacaaag                                                   20

<210> SEQ ID NO 102
<211> LENGTH: 20
<212> TYPE: DNA
<213> ORGANISM: Artificial Sequence
<220> FEATURE:
<223> OTHER INFORMATION: Probe

<400> SEQUENCE: 102
caccaggatg actttgccaa                                                   20

<210> SEQ ID NO 103
<211> LENGTH: 20
<212> TYPE: DNA
<213> ORGANISM: Artificial Sequence

```
<220> FEATURE:
<223> OTHER INFORMATION: Probe

<400> SEQUENCE: 103
ttcagcgcag tgaggaacgg                                               20

<210> SEQ ID NO 104
<211> LENGTH: 20
<212> TYPE: DNA
<213> ORGANISM: Artificial Sequence
<220> FEATURE:
<223> OTHER INFORMATION: Probe

<400> SEQUENCE: 104
gcacaggcgg tcgtgggtct                                               20

<210> SEQ ID NO 105
<211> LENGTH: 20
<212> TYPE: DNA
<213> ORGANISM: Artificial Sequence
<220> FEATURE:
<223> OTHER INFORMATION: Probe

<400> SEQUENCE: 105
gagccgagac aatctctgca                                               20

<210> SEQ ID NO 106
<211> LENGTH: 20
<212> TYPE: DNA
<213> ORGANISM: Artificial Sequence
<220> FEATURE:
<223> OTHER INFORMATION: Probe

<400> SEQUENCE: 106
atctttgtcc agcatgaggt                                               20

<210> SEQ ID NO 107
<211> LENGTH: 20
<212> TYPE: DNA
<213> ORGANISM: Artificial Sequence
<220> FEATURE:
<223> OTHER INFORMATION: Probe

<400> SEQUENCE: 107
aggcgctcgt ggtcctggtt                                               20

<210> SEQ ID NO 108
<211> LENGTH: 20
<212> TYPE: DNA
<213> ORGANISM: Artificial Sequence
<220> FEATURE:
<223> OTHER INFORMATION: Probe

<400> SEQUENCE: 108
caagcaggga cttggcctcg                                               20

<210> SEQ ID NO 109
<211> LENGTH: 20
<212> TYPE: DNA
<213> ORGANISM: Artificial Sequence
<220> FEATURE:
<223> OTHER INFORMATION: Probe

<400> SEQUENCE: 109
ctccggggtc ccacagaagg                                               20
```

```
<210> SEQ ID NO 110
<211> LENGTH: 20
<212> TYPE: DNA
<213> ORGANISM: Artificial Sequence
<220> FEATURE:
<223> OTHER INFORMATION: Probe

<400> SEQUENCE: 110
gacctcggac gtgacctgag                                               20

<210> SEQ ID NO 111
<211> LENGTH: 20
<212> TYPE: DNA
<213> ORGANISM: Artificial Sequence
<220> FEATURE:
<223> OTHER INFORMATION: Probe

<400> SEQUENCE: 111
ctcccgcttg cagtaggaat                                               20

<210> SEQ ID NO 112
<211> LENGTH: 20
<212> TYPE: DNA
<213> ORGANISM: Artificial Sequence
<220> FEATURE:
<223> OTHER INFORMATION: Probe

<400> SEQUENCE: 112
gagtgctcga taaggtggtg                                               20

<210> SEQ ID NO 113
<211> LENGTH: 20
<212> TYPE: DNA
<213> ORGANISM: Artificial Sequence
<220> FEATURE:
<223> OTHER INFORMATION: Probe

<400> SEQUENCE: 113
cacataagtc acatgcatac                                               20

<210> SEQ ID NO 114
<211> LENGTH: 20
<212> TYPE: DNA
<213> ORGANISM: Artificial Sequence
<220> FEATURE:
<223> OTHER INFORMATION: Probe

<400> SEQUENCE: 114
agacaggagt cggagtctgt                                               20

<210> SEQ ID NO 115
<211> LENGTH: 20
<212> TYPE: DNA
<213> ORGANISM: Artificial Sequence
<220> FEATURE:
<223> OTHER INFORMATION: Probe

<400> SEQUENCE: 115
gtagctgctc cagttgggta                                               20

<210> SEQ ID NO 116
<211> LENGTH: 20
<212> TYPE: DNA
<213> ORGANISM: Artificial Sequence
<220> FEATURE:
<223> OTHER INFORMATION: Probe
```

-continued

```
<400> SEQUENCE: 116
atgctgaaca ctgggttagt                                                 20

<210> SEQ ID NO 117
<211> LENGTH: 20
<212> TYPE: DNA
<213> ORGANISM: Artificial Sequence
<220> FEATURE:
<223> OTHER INFORMATION: Probe

<400> SEQUENCE: 117
tatgatctaa actgatgcta                                                 20

<210> SEQ ID NO 118
<211> LENGTH: 20
<212> TYPE: DNA
<213> ORGANISM: Artificial Sequence
<220> FEATURE:
<223> OTHER INFORMATION: Probe

<400> SEQUENCE: 118
ttggtaatga caagtctaaa                                                 20

<210> SEQ ID NO 119
<211> LENGTH: 20
<212> TYPE: DNA
<213> ORGANISM: Artificial Sequence
<220> FEATURE:
<223> OTHER INFORMATION: Probe

<400> SEQUENCE: 119
gagaggagga tcacaattcg                                                 20

<210> SEQ ID NO 120
<211> LENGTH: 20
<212> TYPE: DNA
<213> ORGANISM: Artificial Sequence
<220> FEATURE:
<223> OTHER INFORMATION: Probe

<400> SEQUENCE: 120
tctgctatag atggtgatgt                                                 20

<210> SEQ ID NO 121
<211> LENGTH: 20
<212> TYPE: DNA
<213> ORGANISM: Artificial Sequence
<220> FEATURE:
<223> OTHER INFORMATION: Probe

<400> SEQUENCE: 121
tgaaagatca agaggttcta                                                 20

<210> SEQ ID NO 122
<211> LENGTH: 20
<212> TYPE: DNA
<213> ORGANISM: Artificial Sequence
<220> FEATURE:
<223> OTHER INFORMATION: Probe

<400> SEQUENCE: 122
tgtactactt ctggaaccat                                                 20

<210> SEQ ID NO 123
```

```
<211> LENGTH: 20
<212> TYPE: DNA
<213> ORGANISM: Artificial Sequence
<220> FEATURE:
<223> OTHER INFORMATION: Probe

<400> SEQUENCE: 123
ggctgatcat tgttcttggc                                           20

<210> SEQ ID NO 124
<211> LENGTH: 20
<212> TYPE: DNA
<213> ORGANISM: Artificial Sequence
<220> FEATURE:
<223> OTHER INFORMATION: Probe

<400> SEQUENCE: 124
gagagctctt ctgcacttgg                                           20

<210> SEQ ID NO 125
<211> LENGTH: 20
<212> TYPE: DNA
<213> ORGANISM: Artificial Sequence
<220> FEATURE:
<223> OTHER INFORMATION: Probe

<400> SEQUENCE: 125
gccatctcca gtagctgatg                                           20

<210> SEQ ID NO 126
<211> LENGTH: 20
<212> TYPE: DNA
<213> ORGANISM: Artificial Sequence
<220> FEATURE:
<223> OTHER INFORMATION: Probe

<400> SEQUENCE: 126
aggctgcttt aggtcatagt                                           20

<210> SEQ ID NO 127
<211> LENGTH: 20
<212> TYPE: DNA
<213> ORGANISM: Artificial Sequence
<220> FEATURE:
<223> OTHER INFORMATION: Probe

<400> SEQUENCE: 127
ggacaatcat cacacagaag                                           20

<210> SEQ ID NO 128
<211> LENGTH: 20
<212> TYPE: DNA
<213> ORGANISM: Artificial Sequence
<220> FEATURE:
<223> OTHER INFORMATION: Probe

<400> SEQUENCE: 128
taacagaatg gccaccttgt                                           20

<210> SEQ ID NO 129
<211> LENGTH: 20
<212> TYPE: DNA
<213> ORGANISM: Artificial Sequence
<220> FEATURE:
<223> OTHER INFORMATION: Probe

<400> SEQUENCE: 129
```
atgcaagatt ggcttgatta					20

<210> SEQ ID NO 130
<211> LENGTH: 20
<212> TYPE: DNA
<213> ORGANISM: Artificial Sequence
<220> FEATURE:
<223> OTHER INFORMATION: Probe

<400> SEQUENCE: 130
ccaactgttg gcagaacaac					20

<210> SEQ ID NO 131
<211> LENGTH: 20
<212> TYPE: DNA
<213> ORGANISM: Artificial Sequence
<220> FEATURE:
<223> OTHER INFORMATION: Probe

<400> SEQUENCE: 131
tttaggtgga aataggtaa					20

<210> SEQ ID NO 132
<211> LENGTH: 20
<212> TYPE: DNA
<213> ORGANISM: Artificial Sequence
<220> FEATURE:
<223> OTHER INFORMATION: Probe

<400> SEQUENCE: 132
aacaatgaat atgttcaaca					20

<210> SEQ ID NO 133
<211> LENGTH: 20
<212> TYPE: DNA
<213> ORGANISM: Artificial Sequence
<220> FEATURE:
<223> OTHER INFORMATION: Probe

<400> SEQUENCE: 133
cttacgtgtt atctggagta					20

<210> SEQ ID NO 134
<211> LENGTH: 20
<212> TYPE: DNA
<213> ORGANISM: Artificial Sequence
<220> FEATURE:
<223> OTHER INFORMATION: Probe

<400> SEQUENCE: 134
tggagggata ttctgttcgc					20

<210> SEQ ID NO 135
<211> LENGTH: 20
<212> TYPE: DNA
<213> ORGANISM: Artificial Sequence
<220> FEATURE:
<223> OTHER INFORMATION: Probe

<400> SEQUENCE: 135
tccggacgtg cggtacagag					20

<210> SEQ ID NO 136
<211> LENGTH: 20
<212> TYPE: DNA

<210> SEQ ID NO 137
<211> LENGTH: 20
<212> TYPE: DNA
<213> ORGANISM: Artificial Sequence
<220> FEATURE:
<223> OTHER INFORMATION: Probe

<400> SEQUENCE: 136
caccgagtgg aagttctgct                                        20

<210> SEQ ID NO 137
<211> LENGTH: 20
<212> TYPE: DNA
<213> ORGANISM: Artificial Sequence
<220> FEATURE:
<223> OTHER INFORMATION: Probe

<400> SEQUENCE: 137
ctggttcagg taccacgagg                                        20

<210> SEQ ID NO 138
<211> LENGTH: 20
<212> TYPE: DNA
<213> ORGANISM: Artificial Sequence
<220> FEATURE:
<223> OTHER INFORMATION: Probe

<400> SEQUENCE: 138
gacgacgagc tgctgctggt                                        20

<210> SEQ ID NO 139
<211> LENGTH: 20
<212> TYPE: DNA
<213> ORGANISM: Artificial Sequence
<220> FEATURE:
<223> OTHER INFORMATION: Probe

<400> SEQUENCE: 139
tacaggctca tggcttgcag                                        20

<210> SEQ ID NO 140
<211> LENGTH: 20
<212> TYPE: DNA
<213> ORGANISM: Artificial Sequence
<220> FEATURE:
<223> OTHER INFORMATION: Probe

<400> SEQUENCE: 140
cgcagcgacg tcatgatgtt                                        20

<210> SEQ ID NO 141
<211> LENGTH: 20
<212> TYPE: DNA
<213> ORGANISM: Artificial Sequence
<220> FEATURE:
<223> OTHER INFORMATION: Probe

<400> SEQUENCE: 141
acacatatac ccacctgtgt                                        20

<210> SEQ ID NO 142
<211> LENGTH: 20
<212> TYPE: DNA
<213> ORGANISM: Artificial Sequence
<220> FEATURE:
<223> OTHER INFORMATION: Probe

<400> SEQUENCE: 142
aggtaagtac aacgattaag                                        20

<210> SEQ ID NO 143
<211> LENGTH: 20
<212> TYPE: DNA
<213> ORGANISM: Artificial Sequence
<220> FEATURE:
<223> OTHER INFORMATION: Probe

<400> SEQUENCE: 143
aattatatct cataattgta                                            20

<210> SEQ ID NO 144
<211> LENGTH: 20
<212> TYPE: DNA
<213> ORGANISM: Artificial Sequence
<220> FEATURE:
<223> OTHER INFORMATION: Probe

<400> SEQUENCE: 144
aatggctctg aacaacaaca                                            20

<210> SEQ ID NO 145
<211> LENGTH: 20
<212> TYPE: DNA
<213> ORGANISM: Artificial Sequence
<220> FEATURE:
<223> OTHER INFORMATION: Probe

<400> SEQUENCE: 145
tcaggtcgag cacagcacag                                            20

<210> SEQ ID NO 146
<211> LENGTH: 20
<212> TYPE: DNA
<213> ORGANISM: Artificial Sequence
<220> FEATURE:
<223> OTHER INFORMATION: Probe

<400> SEQUENCE: 146
agctggcatt gccactcacc                                            20

<210> SEQ ID NO 147
<211> LENGTH: 20
<212> TYPE: DNA
<213> ORGANISM: Artificial Sequence
<220> FEATURE:
<223> OTHER INFORMATION: Probe

<400> SEQUENCE: 147
gctcgcatgc tgcactggta                                            20

<210> SEQ ID NO 148
<211> LENGTH: 20
<212> TYPE: DNA
<213> ORGANISM: Artificial Sequence
<220> FEATURE:
<223> OTHER INFORMATION: Probe

<400> SEQUENCE: 148
gctcagcgtc tccaccttgg                                            20

<210> SEQ ID NO 149
<211> LENGTH: 20
<212> TYPE: DNA
<213> ORGANISM: Artificial Sequence
<220> FEATURE:

```
<223> OTHER INFORMATION: Probe

<400> SEQUENCE: 149
ctccttggac acgtccttct                                               20

<210> SEQ ID NO 150
<211> LENGTH: 20
<212> TYPE: DNA
<213> ORGANISM: Artificial Sequence
<220> FEATURE:
<223> OTHER INFORMATION: Probe

<400> SEQUENCE: 150
cgaagcactc gttgagcgag                                               20

<210> SEQ ID NO 151
<211> LENGTH: 20
<212> TYPE: DNA
<213> ORGANISM: Artificial Sequence
<220> FEATURE:
<223> OTHER INFORMATION: Probe

<400> SEQUENCE: 151
cggacccaca ctggtacgtg                                               20

<210> SEQ ID NO 152
<211> LENGTH: 20
<212> TYPE: DNA
<213> ORGANISM: Artificial Sequence
<220> FEATURE:
<223> OTHER INFORMATION: Probe

<400> SEQUENCE: 152
aagctgtgga cactgaggcc                                               20

<210> SEQ ID NO 153
<211> LENGTH: 20
<212> TYPE: DNA
<213> ORGANISM: Artificial Sequence
<220> FEATURE:
<223> OTHER INFORMATION: Probe

<400> SEQUENCE: 153
ccggtacctg ctaaactctc                                               20

<210> SEQ ID NO 154
<211> LENGTH: 20
<212> TYPE: DNA
<213> ORGANISM: Artificial Sequence
<220> FEATURE:
<223> OTHER INFORMATION: Probe

<400> SEQUENCE: 154
actttatagt aatttattat                                               20

<210> SEQ ID NO 155
<211> LENGTH: 20
<212> TYPE: DNA
<213> ORGANISM: Artificial Sequence
<220> FEATURE:
<223> OTHER INFORMATION: Probe

<400> SEQUENCE: 155
ggagagtgac agttgaggga                                               20
```

```
<210> SEQ ID NO 156
<211> LENGTH: 20
<212> TYPE: DNA
<213> ORGANISM: Artificial Sequence
<220> FEATURE:
<223> OTHER INFORMATION: Probe

<400> SEQUENCE: 156
cctgacctct gagcggtgag                                               20

<210> SEQ ID NO 157
<211> LENGTH: 20
<212> TYPE: DNA
<213> ORGANISM: Artificial Sequence
<220> FEATURE:
<223> OTHER INFORMATION: Probe

<400> SEQUENCE: 157
tattcgacta aggctaccca                                               20

<210> SEQ ID NO 158
<211> LENGTH: 20
<212> TYPE: DNA
<213> ORGANISM: Artificial Sequence
<220> FEATURE:
<223> OTHER INFORMATION: Probe

<400> SEQUENCE: 158
ggcatggctg agacacagaa                                               20

<210> SEQ ID NO 159
<211> LENGTH: 20
<212> TYPE: DNA
<213> ORGANISM: Artificial Sequence
<220> FEATURE:
<223> OTHER INFORMATION: Probe

<400> SEQUENCE: 159
ctggtcttac aaatggactc                                               20

<210> SEQ ID NO 160
<211> LENGTH: 20
<212> TYPE: DNA
<213> ORGANISM: Artificial Sequence
<220> FEATURE:
<223> OTHER INFORMATION: Probe

<400> SEQUENCE: 160
taatggcaga gtggagtagt                                               20

<210> SEQ ID NO 161
<211> LENGTH: 20
<212> TYPE: DNA
<213> ORGANISM: Artificial Sequence
<220> FEATURE:
<223> OTHER INFORMATION: Probe

<400> SEQUENCE: 161
caacatctca gtttcataca                                               20

<210> SEQ ID NO 162
<211> LENGTH: 20
<212> TYPE: DNA
<213> ORGANISM: Artificial Sequence
<220> FEATURE:
<223> OTHER INFORMATION: Probe
```

<400> SEQUENCE: 162
attgcatttg tggtatgcat                                               20

<210> SEQ ID NO 163
<211> LENGTH: 20
<212> TYPE: DNA
<213> ORGANISM: Artificial Sequence
<220> FEATURE:
<223> OTHER INFORMATION: Probe

<400> SEQUENCE: 163
agacaatgga gcatgcgcca                                               20

<210> SEQ ID NO 164
<211> LENGTH: 20
<212> TYPE: DNA
<213> ORGANISM: Artificial Sequence
<220> FEATURE:
<223> OTHER INFORMATION: Probe

<400> SEQUENCE: 164
acctgagttc gcgtctggca                                               20

<210> SEQ ID NO 165
<211> LENGTH: 20
<212> TYPE: DNA
<213> ORGANISM: Artificial Sequence
<220> FEATURE:
<223> OTHER INFORMATION: Probe

<400> SEQUENCE: 165
tctctcaatc tagccatcag                                               20

<210> SEQ ID NO 166
<211> LENGTH: 20
<212> TYPE: DNA
<213> ORGANISM: Artificial Sequence
<220> FEATURE:
<223> OTHER INFORMATION: Probe

<400> SEQUENCE: 166
tgcattctgt tcgagtaaac                                               20

<210> SEQ ID NO 167
<211> LENGTH: 20
<212> TYPE: DNA
<213> ORGANISM: Artificial Sequence
<220> FEATURE:
<223> OTHER INFORMATION: Probe

<400> SEQUENCE: 167
ttgtgcagga gagacattct                                               20

<210> SEQ ID NO 168
<211> LENGTH: 20
<212> TYPE: DNA
<213> ORGANISM: Artificial Sequence
<220> FEATURE:
<223> OTHER INFORMATION: Probe

<400> SEQUENCE: 168
gtctgcaaat gctctgttgc                                               20

<210> SEQ ID NO 169
<211> LENGTH: 20

```
<212> TYPE: DNA
<213> ORGANISM: Artificial Sequence
<220> FEATURE:
<223> OTHER INFORMATION: Probe

<400> SEQUENCE: 169
tccgaatatg catcttcagg                                          20

<210> SEQ ID NO 170
<211> LENGTH: 21
<212> TYPE: DNA
<213> ORGANISM: Artificial Sequence
<220> FEATURE:
<223> OTHER INFORMATION: Probe

<400> SEQUENCE: 170
gcttggactg tagtctttcc t                                        21

<210> SEQ ID NO 171
<211> LENGTH: 20
<212> TYPE: DNA
<213> ORGANISM: Artificial Sequence
<220> FEATURE:
<223> OTHER INFORMATION: Probe

<400> SEQUENCE: 171
gaagtgctgc aatgtgtcat                                          20

<210> SEQ ID NO 172
<211> LENGTH: 20
<212> TYPE: DNA
<213> ORGANISM: Artificial Sequence
<220> FEATURE:
<223> OTHER INFORMATION: Probe

<400> SEQUENCE: 172
acatgactgt ctccatgaca                                          20

<210> SEQ ID NO 173
<211> LENGTH: 20
<212> TYPE: DNA
<213> ORGANISM: Artificial Sequence
<220> FEATURE:
<223> OTHER INFORMATION: Probe

<400> SEQUENCE: 173
gaagttgaag ctggaaatac                                          20

<210> SEQ ID NO 174
<211> LENGTH: 20
<212> TYPE: DNA
<213> ORGANISM: Artificial Sequence
<220> FEATURE:
<223> OTHER INFORMATION: Probe

<400> SEQUENCE: 174
gagtcgcata agaattgcga                                          20

<210> SEQ ID NO 175
<211> LENGTH: 20
<212> TYPE: DNA
<213> ORGANISM: Artificial Sequence
<220> FEATURE:
<223> OTHER INFORMATION: Probe

<400> SEQUENCE: 175
```
aggaagactt tttctggctg                                                    20

<210> SEQ ID NO 176
<211> LENGTH: 20
<212> TYPE: DNA
<213> ORGANISM: Artificial Sequence
<220> FEATURE:
<223> OTHER INFORMATION: Probe

<400> SEQUENCE: 176
cctataaagg aagctcgaaa                                                    20

<210> SEQ ID NO 177
<211> LENGTH: 20
<212> TYPE: DNA
<213> ORGANISM: Artificial Sequence
<220> FEATURE:
<223> OTHER INFORMATION: Probe

<400> SEQUENCE: 177
aatgccagct atattgatgg                                                    20

<210> SEQ ID NO 178
<211> LENGTH: 20
<212> TYPE: DNA
<213> ORGANISM: Artificial Sequence
<220> FEATURE:
<223> OTHER INFORMATION: Probe

<400> SEQUENCE: 178
ggaaatacat tgctgcacaa                                                    20

<210> SEQ ID NO 179
<211> LENGTH: 20
<212> TYPE: DNA
<213> ORGANISM: Artificial Sequence
<220> FEATURE:
<223> OTHER INFORMATION: Probe

<400> SEQUENCE: 179
ttgctcctca aactgagaag                                                    20

<210> SEQ ID NO 180
<211> LENGTH: 20
<212> TYPE: DNA
<213> ORGANISM: Artificial Sequence
<220> FEATURE:
<223> OTHER INFORMATION: Probe

<400> SEQUENCE: 180
gatgcctgat ggttcaagta                                                    20

<210> SEQ ID NO 181
<211> LENGTH: 24
<212> TYPE: DNA
<213> ORGANISM: Artificial Sequence
<220> FEATURE:
<223> OTHER INFORMATION: Probe

<400> SEQUENCE: 181
gtagcttagt ctgaagtcaa tact                                               24

<210> SEQ ID NO 182
<211> LENGTH: 24
<212> TYPE: DNA
<213> ORGANISM: Artificial Sequence

```
<220> FEATURE:
<223> OTHER INFORMATION: Probe

<400> SEQUENCE: 182
attcatgact atattctgta gcaa                                          24

<210> SEQ ID NO 183
<211> LENGTH: 24
<212> TYPE: DNA
<213> ORGANISM: Artificial Sequence
<220> FEATURE:
<223> OTHER INFORMATION: Probe

<400> SEQUENCE: 183
gtcaatgatg atcttggtat cttg                                          24

<210> SEQ ID NO 184
<211> LENGTH: 24
<212> TYPE: DNA
<213> ORGANISM: Artificial Sequence
<220> FEATURE:
<223> OTHER INFORMATION: Probe

<400> SEQUENCE: 184
agtattgact tcagactaag ctac                                          24

<210> SEQ ID NO 185
<211> LENGTH: 24
<212> TYPE: DNA
<213> ORGANISM: Artificial Sequence
<220> FEATURE:
<223> OTHER INFORMATION: Probe

<400> SEQUENCE: 185
ttgctacaga atatagtcat gaat                                          24

<210> SEQ ID NO 186
<211> LENGTH: 24
<212> TYPE: DNA
<213> ORGANISM: Artificial Sequence
<220> FEATURE:
<223> OTHER INFORMATION: Probe

<400> SEQUENCE: 186
caagatacca agatcatcat tgac                                          24

<210> SEQ ID NO 187
<211> LENGTH: 24
<212> TYPE: DNA
<213> ORGANISM: Artificial Sequence
<220> FEATURE:
<223> OTHER INFORMATION: Probe

<400> SEQUENCE: 187
gtacgtcgta atttgaatct gtag                                          24

<210> SEQ ID NO 188
<211> LENGTH: 24
<212> TYPE: DNA
<213> ORGANISM: Artificial Sequence
<220> FEATURE:
<223> OTHER INFORMATION: Probe

<400> SEQUENCE: 188
gctgtgaatg taacatgtct atcg                                          24
```

<210> SEQ ID NO 189
<211> LENGTH: 24
<212> TYPE: DNA
<213> ORGANISM: Artificial Sequence
<220> FEATURE:
<223> OTHER INFORMATION: Probe

<400> SEQUENCE: 189
gtcagttaga ctattgttcg ttcg					24

<210> SEQ ID NO 190
<211> LENGTH: 24
<212> TYPE: DNA
<213> ORGANISM: Artificial Sequence
<220> FEATURE:
<223> OTHER INFORMATION: Probe

<400> SEQUENCE: 190
ctacagattc aaattacgac gtac					24

<210> SEQ ID NO 191
<211> LENGTH: 24
<212> TYPE: DNA
<213> ORGANISM: Artificial Sequence
<220> FEATURE:
<223> OTHER INFORMATION: Probe

<400> SEQUENCE: 191
cgatagacat gttacattca cagc					24

<210> SEQ ID NO 192
<211> LENGTH: 24
<212> TYPE: DNA
<213> ORGANISM: Artificial Sequence
<220> FEATURE:
<223> OTHER INFORMATION: Probe

<400> SEQUENCE: 192
cgaacgaaca atagtctaac tgac					24